(12) United States Patent
Henley et al.

(10) Patent No.: US 7,016,724 B2
(45) Date of Patent: Mar. 21, 2006

(54) ELECTROKINETIC DELIVERY SYSTEM FOR SELF-ADMINISTRATION OF MEDICAMENTS AND METHODS THEREFOR

(75) Inventors: Julian L. Henley, New Haven, CT (US); Kuo Wei Chang, Waltham, MA (US); Joseph Potter, Oak Bluffs, MA (US); Dennis I. Goldberg, South Brookline, MA (US)

(73) Assignee: Transport Pharmaceuticals, Inc., West Conshohocken, PA (US)

( * ) Notice: Subject to any disclaimer, the term of this patent is extended or adjusted under 35 U.S.C. 154(b) by 17 days.

(21) Appl. No.: 10/724,160

(22) Filed: Dec. 1, 2003

(65) Prior Publication Data

US 2004/0111051 A1   Jun. 10, 2004

Related U.S. Application Data

(60) Division of application No. 10/117,346, filed on Apr. 8, 2002, now Pat. No. 6,792,306, which is a continuation-in-part of application No. 09/584,138, filed on May 31, 2000, now Pat. No. 6,477,410, and a continuation-in-part of application No. 09/523,217, filed on Mar. 10, 2000, now Pat. No. 6,553,253.

(51) Int. Cl.
*A61N 1/30*   (2006.01)
(52) U.S. Cl. .......................... 604/20; 604/501
(58) Field of Classification Search ............ 604/19–21, 604/501; 607/148, 149, 152, 153
See application file for complete search history.

(56) References Cited

U.S. PATENT DOCUMENTS

| | | | |
|---|---|---|---|
| 206,474 A | 7/1878 | Morel | |
| 279,524 A | 6/1883 | Beaty | 607/145 |
| 484,522 A | 10/1892 | McBride | |
| 600,290 A | 3/1898 | Muir | |
| 1,967,927 A | 7/1934 | Deustch | 604/20 |
| 2,047,308 A | 7/1936 | Chapman | 128/799 |

(Continued)

FOREIGN PATENT DOCUMENTS

AT   OE 0232642   3/1964   .................. 604/20

(Continued)

OTHER PUBLICATIONS

"Iontophoretic Treatment of Oral Herpes," Henley et al.; Laryngoscope, vol. 94, No. 1, pp. 118-121, Jan. 1984.

(Continued)

*Primary Examiner*—Henry Bennett
*Assistant Examiner*—Camtu Nguyen
(74) *Attorney, Agent, or Firm*—Nixon & Vanderhye P.C.

(57) ABSTRACT

An electrokinetic delivery system for personal use in self-administration of a medicament to a treatment site on an individual includes a device shaped to conform with the shape of a portion of an individual's finger from a tip thereof to a location past the first finger joint. A self-contained power source is carried by the device and a first electrode is carried by the device adjacent a distal end portion thereof and the tip of the individual's finger. The first electrode is in electrical contact with the power source. A second electrode is carried by the device for contact with the individual's finger. The second electrode is in electrical contact with the power source. Upon application of the first electrode over a treatment site with the medicament disposed between the first electrode and the treatment site and completion of an electrical circuit through the individual's body and said electrode, the device applies current for electrokinetically driving the medicament into the treatment site.

22 Claims, 21 Drawing Sheets

U.S. PATENT DOCUMENTS

| | | |
|---|---|---|
| 2,123,980 A | 7/1938 | Warwick |
| 2,126,070 A | 8/1938 | Wappler |
| 2,834,344 A | 5/1958 | Kanai |
| 3,019,787 A | 2/1962 | Simmons |
| 3,048,170 A | 8/1962 | Lemos |
| 3,107,672 A | 10/1963 | Hofmann |
| 3,163,166 A | 12/1964 | Brant et al. |
| 3,298,368 A | 1/1967 | Charos ................. 128/260 |
| 3,520,297 A | 7/1970 | Bechtold |
| 3,556,105 A | 1/1971 | Shepard |
| 3,645,260 A | 2/1972 | Cinotti et al. |
| 3,716,054 A | 2/1973 | Porter et al. |
| 3,831,598 A | 8/1974 | Tice |
| 3,848,600 A | 11/1974 | Patrick, Jr. et al. ......... 128/783 |
| 4,116,238 A | 9/1978 | Pettijohn ................. 128/172.1 |
| 4,166,457 A | 9/1979 | Jacobsen et al. |
| 4,211,222 A | 7/1980 | Tapper ................. 128/803 |
| 4,292,968 A | 10/1981 | Ellis ................. 128/207.21 |
| 4,301,794 A | 11/1981 | Tapper ................. 604/20 |
| 4,325,367 A | 4/1982 | Tapper |
| 4,383,529 A | 5/1983 | Webster |
| 4,393,884 A | 7/1983 | Jacobs ................. 131/273 |
| 4,406,658 A | 9/1983 | Lattin et al. ................. 604/20 |
| 4,416,274 A | 11/1983 | Jacobsen et al. ................. 128/803 |
| 4,429,703 A | 2/1984 | Haber ................. 131/273 |
| 4,474,570 A | 10/1984 | Ariura et al. ................. 604/20 |
| 4,510,939 A | 4/1985 | Brenman et al. ................. 128/639 |
| 4,639,244 A | 1/1987 | Rizk et al. |
| 4,655,229 A | 4/1987 | Sensabaugh, Jr. et al. ... 131/273 |
| 4,665,921 A | 5/1987 | Teranishi et al. |
| 4,689,039 A | 8/1987 | Masaki |
| 4,702,732 A | 10/1987 | Powers et al. |
| 4,708,716 A | 11/1987 | Sibalis ................. 604/20 |
| 4,735,217 A | 4/1988 | Gerth et al. ................. 131/273 |
| 4,747,819 A | 5/1988 | Phipps et al. |
| 4,756,318 A | 7/1988 | Clearman et al. ................. 131/359 |
| 4,763,660 A | 8/1988 | Kroll et al. ................. 128/798 |
| 4,764,164 A | 8/1988 | Sasaki ................. 604/20 |
| 4,767,402 A | 8/1988 | Kost et al. |
| 4,771,796 A | 9/1988 | Myer ................. 131/273 |
| 4,776,353 A | 10/1988 | Lilja et al. ................. 131/297 |
| 4,786,278 A | 11/1988 | Masaki ................. 604/20 |
| 4,787,888 A | 11/1988 | Fox |
| 4,793,366 A | 12/1988 | Hill ................. 131/273 |
| 4,800,903 A | 1/1989 | Ray et al. ................. 131/273 |
| 4,808,152 A | 2/1989 | Sibalis ................. 604/20 |
| 4,813,437 A | 3/1989 | Ray ................. 131/273 |
| 4,820,263 A | 4/1989 | Spevak et al. ................. 604/20 |
| 4,821,740 A | 4/1989 | Tachibana et al. ................. 604/20 |
| 4,838,273 A | 6/1989 | Cartmell ................. 600/392 |
| 4,865,582 A | 9/1989 | Sibalis ................. 604/20 |
| 4,907,606 A | 3/1990 | Lilja et al. ................. 131/273 |
| 4,913,148 A | 4/1990 | Diethelm |
| 4,917,119 A | 4/1990 | Potter et al. ................. 131/273 |
| 4,919,648 A | 4/1990 | Sibalis ................. 604/20 |
| 4,922,901 A | 5/1990 | Brooks et al. ......... 128/203.26 |
| 4,931,046 A | 6/1990 | Newman ................. 604/20 |
| 4,942,883 A | 7/1990 | Newman ................. 604/20 |
| 4,950,229 A | 8/1990 | Sage, Jr. ................. 604/20 |
| 4,953,565 A | 9/1990 | Tachibana et al. ................. 604/20 |
| 4,957,480 A | 9/1990 | Morenings |
| 4,979,938 A | 12/1990 | Stephen et al. |
| 4,997,418 A | 3/1991 | DeMartini |
| 5,002,527 A | 3/1991 | Reller et al. |
| 5,006,108 A | 4/1991 | LaPrade ................. 604/20 |
| 5,019,034 A | 5/1991 | Weaver et al. ................. 604/20 |
| 5,037,381 A | 8/1991 | Bock et al. |
| 5,042,975 A | 8/1991 | Chien et al. |
| 5,047,007 A | 9/1991 | McNichols et al. ........... 604/20 |
| 5,053,001 A | 10/1991 | Reller et al. ................. 604/20 |
| 5,060,671 A | 10/1991 | Counts et al. ................. 131/329 |
| 5,090,402 A | 2/1992 | Bazin et al. |
| 5,115,805 A | 5/1992 | Bommannan et al. |
| 5,133,352 A | 7/1992 | Lathrop et al. |
| 5,135,478 A | 8/1992 | Sibalis |
| 5,135,479 A | 8/1992 | Sibalis et al. ................. 604/20 |
| 5,147,291 A | 9/1992 | Cukier ................. 604/22 |
| 5,160,316 A | 11/1992 | Henley ................. 604/20 |
| 5,162,042 A | 11/1992 | Gyory et al. |
| 5,167,242 A | 12/1992 | Turner et al. ................. 131/273 |
| 5,169,384 A | 12/1992 | Bosniak et al. |
| 5,171,215 A | 12/1992 | Flanagan ................. 604/20 |
| 5,203,768 A | 4/1993 | Haak et al. |
| 5,250,022 A | 10/1993 | Chien et al. |
| 5,254,081 A | 10/1993 | Maurer et al. ................. 604/20 |
| 5,279,543 A | 1/1994 | Glikfeld et al. |
| 5,284,471 A | 2/1994 | Sage, Jr. |
| 5,298,017 A | 3/1994 | Theeuwes et al. |
| 5,310,404 A | 5/1994 | Gyory et al. |
| 5,312,326 A | 5/1994 | Myers et al. |
| 5,314,502 A | 5/1994 | McNichols et al. |
| 5,331,979 A | 7/1994 | Henley |
| 5,354,321 A | 10/1994 | Berger |
| 5,360,440 A | 11/1994 | Andersen |
| 5,362,307 A | 11/1994 | Guy et al. |
| 5,362,308 A | 11/1994 | Chien et al. |
| 5,374,241 A | 12/1994 | Lloyd et al. |
| 5,374,242 A | 12/1994 | Haak et al. |
| 5,376,107 A | 12/1994 | Inagi et al. |
| 5,391,195 A | 2/1995 | Van Groningen |
| 5,395,310 A | 3/1995 | Untereker et al. |
| 5,413,590 A | 5/1995 | Williamson |
| 5,415,629 A | 5/1995 | Henley |
| 5,421,816 A | 6/1995 | Lipkovker |
| 5,441,936 A | 8/1995 | Houghten et al. |
| 5,443,441 A | 8/1995 | De Claviere |
| 5,458,569 A | 10/1995 | Kirk, III et al. ................. 604/20 |
| 5,464,387 A | 11/1995 | Haak et al. |
| 5,466,217 A | 11/1995 | Myers et al. |
| 5,470,349 A | 11/1995 | Kleditsch et al. |
| 5,494,679 A | 2/1996 | Sage, Jr. et al. |
| 5,501,705 A | 3/1996 | Fakhri |
| 5,514,167 A | 5/1996 | Smith et al. |
| 5,538,503 A | 7/1996 | Henley |
| 5,540,669 A | 7/1996 | Sage, Jr. et al. ................. 604/20 |
| 5,551,953 A | 9/1996 | Lattin et al. |
| 5,558,632 A | 9/1996 | Lloyd et al. |
| 5,562,607 A | 10/1996 | Gyory |
| 5,589,563 A | 12/1996 | Ward et al. |
| 5,603,693 A | 2/1997 | Frenkel et al. |
| 5,607,461 A | 3/1997 | Lathrop |
| 5,607,691 A | 3/1997 | Hale et al. |
| 5,618,275 A | 4/1997 | Bock |
| 5,658,247 A | 8/1997 | Henley |
| 5,667,487 A | 9/1997 | Henley |
| 5,668,170 A | 9/1997 | Gyory |
| 5,676,648 A | 10/1997 | Henley |
| 5,678,273 A | 10/1997 | Porcelli |
| 5,688,233 A | 11/1997 | Hofmann et al. |
| 5,697,896 A | 12/1997 | McNichols et al. |
| 5,700,457 A | 12/1997 | Dixon |
| 5,711,761 A | 1/1998 | Untereker et al. |
| 5,713,846 A | 2/1998 | Bernhard et al. |
| 5,722,397 A | 3/1998 | Eppstein |
| 5,725,817 A | 3/1998 | Milder |
| 5,733,255 A | 3/1998 | Dinh et al. |
| 5,755,750 A | 5/1998 | Petruska et al. |
| 5,788,666 A | 8/1998 | Atanasoska |
| 5,794,774 A | 8/1998 | Porcelli |
| 5,795,321 A | 8/1998 | McArthur et al. |
| 5,797,867 A | 8/1998 | Guerrara et al. |
| 5,830,175 A | 11/1998 | Flower |
| 5,840,057 A | 11/1998 | Aloisi |
| 5,846,217 A | 12/1998 | Beck et al. |

| | | |
|---|---|---|
| 5,865,786 A | 2/1999 | Sibalis et al. ............... 604/20 |
| 5,879,323 A | 3/1999 | Henley |
| 5,882,676 A | 3/1999 | Lee et al. |
| 5,899,875 A | 5/1999 | Millot |
| 5,899,876 A | 5/1999 | Flower ............... 604/20 |
| 5,908,401 A | 6/1999 | Henley ............... 604/20 |
| 5,911,319 A | 6/1999 | Porcelli et al. |
| 5,919,155 A | 7/1999 | Lattin et al. ............... 604/20 |
| 5,931,859 A | 8/1999 | Burke |
| 5,935,598 A | 8/1999 | Sage et al. |
| 5,954,684 A | 9/1999 | Flower et al. ............... 604/20 |
| 5,961,482 A | 10/1999 | Chien et al. |
| 5,961,483 A | 10/1999 | Sage et al. |
| 5,968,005 A | 10/1999 | Tu |
| 5,968,006 A | 10/1999 | Hofmann |
| 5,983,130 A | 11/1999 | Phipps et al. |
| 6,004,309 A | 12/1999 | Phipps |
| 6,004,547 A | 12/1999 | Rowe et al. |
| 6,006,130 A | 12/1999 | Higo et al. |
| 6,018,679 A | 1/2000 | Dinh et al. |
| 6,023,639 A | 2/2000 | Hakky et al. |
| 6,032,073 A | 2/2000 | Effenhauser |
| 6,038,485 A | 3/2000 | Axelgaard |
| 6,041,252 A | 3/2000 | Walker et al. |
| 6,041,253 A | 3/2000 | Kost et al. |
| 6,048,545 A | 4/2000 | Keller et al. |
| 6,057,374 A | 5/2000 | Huntington et al. |
| 6,101,411 A | 8/2000 | Newsome |
| 6,148,231 A | 11/2000 | Henley ............... 604/20 |
| 6,148,232 A | 11/2000 | Avrahami ............... 604/20 |
| 6,167,302 A | 12/2000 | Millot |
| 6,267,736 B1 | 7/2001 | McCambridge et al. |
| 6,385,487 B1 | 5/2002 | Henley ............... 604/20 |
| 6,477,410 B1 | 11/2002 | Henley et al. |

FOREIGN PATENT DOCUMENTS

| | | | |
|---|---|---|---|
| EP | 0230749 | 8/1987 | ............... 604/20 |
| EP | 0309093 A1 | 3/1989 | ............... 604/20 |
| EP | 617979 A1 | 10/1994 | |
| FR | 1445703 | 6/1966 | ............... 604/20 |
| FR | 2 513 129 | 3/1983 | |
| GB | 0299553 | 11/1928 | ............... 604/20 |
| JP | 3-170172 | 7/1991 | |
| SU | 654254 | 3/1979 | |
| SU | 931191 | 5/1982 | |
| SU | 1003853 | 3/1983 | |
| WO | 07269 | 12/1986 | ............... 604/20 |
| WO | WO 90/06153 | 6/1990 | |
| WO | 08571 | 8/1990 | ............... 604/20 |
| WO | 03790 | 3/1993 | ............... 604/20 |

OTHER PUBLICATIONS

"Iontophoretic Application of Idoxuridine for Recurrent Herpes Libialis: Report of Preliminary Chemical Trials," Gangarosa et al.; Meth. And Find. Exptl. Clin. Pharmacol. 1(2), pp. 105-109 (1979).

"Iontophoresis of Vidarabine Monophosphate for Herpes Orolabialis," Gangarosa et al.; The Journal of Infectious Diseases, vol. 154, No. 6, pp. 930-934, Dec. 1986.

"The Natural History of Recurrent Herpes Simplex Labialis," Spruance et al.; The New England Journal of Medicine, vol. 297, No. 2, pp. 69-75, Jul. 14, 1977.

"Infection with Herpes-Simplex Viruses 1 and 2," Nahmias et al.; The New England Journal of Medicine, pp. 667-674, Sep. 27, 1973.

"Anesthesia of the Human Tympanic Membrane by Iontophoresis of a Local Anesthetic," Comeau et al.; The Laryngoscope, 88:1978, pp. 277-285.

"Iontophoretic Application of Drugs," Waud, J. Appl. Physiol. 23(1), 1967, pp. 128-130.

"Antibiotic Iontophoresis in the Treatment of Ear Chondritis," LaForest et al., Physical Therapy, vol. 58, No. 1, Jan. 1978, pp. 32-34.

"The Quantity and Distribution of Radiolabeled Dexamethasone Delivered to Tissue by Iontophoresis," Glass et al.; International Journal of Dermatology, vol. 19, Nov. 1980, pp. 519-525.

"Iontophoretic Application of Antiviral Chemotherapeutic Agents," Hill et al., Annals New York Academy of Sciences, pp. 604-612.

"Ocular Iontophoresis," Hill et al. Paper, Louisiana State University Medical Center, School of Medicine, New Orleans, Louisiana, pp. 331-354.

"Iontophoretic Application of Adenine Arabinoside Monophosphate to Herpes Simplex Virus Type 1-Infected Hairless Mouse Skin," Park et al.; Antimicrobial Agents and Chemotherapy, vol. 14, No. 4, Oct., 1978, pp. 605-608.

"Iontophoresis: Applications in Transdermal Medication Delivery," Costello et al.; Physical Therapy, vol. 75, No. 6, pp. 104/554-113/563, Jun. 1995.

Physical Enhancement of Dermatologic Drug Delivery: Iontophoresis and Phonophoresis, Kassan et al., Journal of the American Academy of Dermatology, Apr. 1996, pp. 657-666.

"Iontophoresis and Herpes Labialis," Boxhall et al.; The Medical Journal of Australia, May 26, 1984, pp. 686-687.

"Iontophoresis: A Method of Antibiotic Administration in the Burn Patient," Rapperport et al., Plastic and Reconstructive Surgery, 1965, vol. 36, No. 5, pp. 547-552.

"Iontophoresis for Enhancing Penetration of Dermatologic and Antiviral Drugs," Gangarosa et al., Journal of Dermatology, vol. 22, No. 11, pp. 865-875, Nov. 1995.

"Iontophoretic Treatment of Herpetic Whitlow," Gangarosa et al., Arch. Phys. Med. Rehabil., vol. 70, pp. 336-340Apr. 1989.

"Iontophoretic Application of Antiviral Drugs," Gangarosa et al., Proceedings of an International Symposium held in Tokushima City, Japan, pp. 201-204, Jul. 27-30, 1981.

"Iontophoretic Application of Adenine Arabinoside Monophosphate for the Treatment of Herpes Simplex Virus Type 2 Skin Infections in Hairless Mice," Gangarosa, The Journal of Infectious Diseases, vol. 140, No. 6, pp. 1014, Dec. 1979.

"Effect of Iontophoretic and Topical Application of Antiviral Agents in Treatment of Experimental HSV-1 Keratitis in Rabbits," Kwon et al., Investigative Ophthalmology & Visual Science, vol. 18, No. 9, pp. 984-988, Sep., 1979.

"Acyclovir and Vidarabine Monophosphate: Comparison of Iontophoretic and Intravenous Administration for the Treatment of HSV-1 Stromal Keratitis," Hill et al., The American Journal of Medicine, Acyclovir Symposium, pp. 300-304.

"Thymine Arabinoside (Ara-T) Topical and Iontophoretic Applications for Herpes Simplex Virus Type 1 and Type 2 Skin Infections in Hairless Mice," Hill et al., Meth. And Find. Exptl. Clin. Pharmacol. 6(1), pp. 17-20, 1984.

"Iontophoresis Enhances the Transport of Acyclovir Through Nude Mouse Skin by Electrorepulsion and Electroosmosis," Volpato et al., Pharmaceutical Research, vol. 12, No. 11, pp. 1623-1627, 1995.

"Early Application of Topical 15% Idoxuridine n Dimethyl Sulfoxide Shortens the Course of Herpes Simplex Labialis: A Multicenter Placebo-Controlled Trial," Spruance et al., The Journal of Infectious Diseases, 1990; vol. 161; pp. 191-197.

"Iontophoresis for Surface Level Anesthesia," Gangarosa, JADA, vol. 88, pp. 125-128, Jan. 1974.

"Conductivity of Drugs Used for Iontophoresis," Gangarosa et al., Journal of Pharmaceutical Sciences, vol. 67, No. 10, pp. 1439-1443, Oct., 1978.

"A Pilot Study of Iontophoretic Cisplatin Chemotherapy of Basal and Squamous Cell Carcinomas of the Skin," Chang et al., Arch. Dermatol., vol. 129, pp. 425-427, Apr. 1993.

"How Modern Iontophoresis Can Improve Your Practice," Gangarosa et al., (Quintessence International) Oral Surgery, No. 10, Report 2135, Oct. 1982, pp. 1027-1038.

"Postherpetic Neuralgia," Baron et al., Brain (1993), 116, pp. 1477-1496.

"Iontophoretic Assistance of 5-Iodo-2'-Deoxyuridine Penetration into Neonatal Mouse Skin and Effects of DNA Synthesis," Gangarosa et al., Society for Experimental Biology and Medicine, pp. 439-443, 1997.

"Electrophoretic Evaluation of the Mobility of Drugs Suitable for Iontophoresis," Kamath et al., Meth. Find. Exp. Clin. Pharmacol., 1995, 17(4): pp. 227-232.

"Transdermal Drug Delivery by Passive Diffusion and Iontophoresis: A Review," Singh et al., Medicinal Research Reviews, vol. 13, No. 5, 1993, pp. 569-621.

"Iontophoresis: Electrorepulsion and Electroosmosis," Guy et al., Journal of Controlled Release 64 (2000) 129-132.

"Treatment of Common Cutaneous Herpes Simplex Virus Infections," Emmert, American Family Physician, vol. 61, No. 6, Mar. 15, 2000, pp. 1697-1704.

"Gelatin-stabilised Microemulsion-Based Oranogels: Rheology and Application in Iontophoretic Transdermal Drug Delivery," Kantaria et al., Journal of Controlled Release 60 (1999) 355-365.

"Electrorepulsion Versus Electroosmosis: Effect of pH on the Iontophoretic Flux of 5-Fluorouracil," Merino et al., Pharmaceutical Research, vol. 16, No. 6 (1999).

"Azelaic Acid: Potential as a General Antitumoural Agent," Breathnach, Medical Hypotheses (1999) 52(3) 221-226.

"Treatment of Mucocutaneous Herpes Simplex Virus Infections Unresponsive to Acyclovir with Topical Foscarnet Cream in AIDS Patients: A Phase I/II Study," Javaly et al., Journal of Acquired Immune Deficiency Syndromes 21:301-306.

"Efficacy and Safety of Azelaic Acid and Glycolic Acid Combination Therapy Compared with Tretinoin Therapy for Acne," Spellman et al., Clinical Therapeutics, vol. 20, No. 4, 1998, pp. 711-721.

"Passive Versus Electrotransport-Facilitated Transdermal Absorption of Ketorolac," Park et al., Clinical Pharmacology & Therapeutics, vol. 63, No. 3, pp. 303-315.

"Soriudine Versus Acyclovir for Treatment of Dermatomal Herpes Zoster in Human Immunodeficiency Virus-Infected Patients: Results from a Randomized, Controlled Clinical Trial," Gnann et al., Antimicrobial Agents and Chemotherapy, vol. 42, No. 5, May 1998, pp. 1139-1145.

"Azelaic Acid 20% Cream (AZELEX®) and the Medical Management of Acne Vulgaris," Gibson, Dermatology Nursing, vol. 9, No. 5, pp. 339-344.

"Sorivudine: A Promising Drug for the Treatment of Varicella-Zoster Virus Infection," Whitley, Neurology 1995; 45 (Supp. 8), pp. S73-S75.

"Antiherpesviral and Anticellular Effects of 1-β-D-Arabinofuranosyl-E-5-(2-Halogenovinyl) Uracils," Machida et al., Antimicrobial Agents and Chemotherapy, Jul. 1981, pp. 47-52.

"Herpes Simplex," American Academy of Dermatology, 1987, Revised 1991, 1993.

"'Common Cold' Virus is Near," Haney, The Associated Press, Jan. 15, 2000.

"New Medicines Move to Eradicate Acne," Hemphill, The New York Times, Feb. 29, 2000.

"Warts," American Academy of Dermatology, American Academy of Dermatology, 1997, Revised 1991, 1993.

"Psoriasis," American Academy of Dermatology, 1994.

"Eczema/Atopic Dermatitis," American Academy of Dermatology, 1987, Revised 1991, 1993, 1995.

"Skin Cancer: An Undeclared Epidemic," American Academy of Dermatology, 1988, Revised 1989, 1993, 1994.

"Electrophoretically Controlled Dermal or Transdermal Application Systems with Electronic Indicators," Gröning, International Journal of Pharmaceutics, 36 (1987) pp. 37-40.

ELECTROKINETIC DELIVERY SYSTEM FOR SELF-ADMINISTRATION OF MEDICAMENTS AND METHODS THEREFOR

RELATED APPLICATIONS

This application is a division of application Ser. No. 10/117,346, filed Apr. 8, 2002, now U.S. Pat. No. 6,792,306 which is a continuation-in-part of application Ser. No. 09/584,138, filed May 31, 2000, now U.S. Pat. No. 6,477,410, issued Nov. 5, 2002 and is a continuation-in-part of application Ser. No. 09/523,217, filed Mar. 10, 2000, now U.S. Pat. No. 6,553,253, issued Apr. 22, 2003, the disclosures of which are incorporated herein by reference.

BACKGROUND OF THE INVENTION

The present invention relates generally to the electrokinetic mass transfer of substances into and/or extracting substances from tissue and particularly to apparatus and methods for extracting, e.g., body fluids and/or harmful substances from a site, and/or delivering substances, e.g., a medicament to a treatment site.

Electrokinetic delivery of medicaments for applying medication locally through an individual's skin is known. One type of electrokinetic delivery mechanism is iontophoresis, i.e., the application of an electric field to the skin to enhance the skin's permeability and to deliver various ionic agents, e.g., ions of soluble salts or other drugs. In certain situations, iontophoretic transdermal or transmucocutaneous delivery techniques have obviated the need for hypodermic injection for many medicaments, thereby eliminating the concomitant problem of trauma, pain and risk of infection to the individual. Other types of electrokinetic delivery mechanisms include electroosmosis, electroporation, electromigration, electrophoresis and endosmose, any or all of which are generally known as electrotransport, electromolecular transport or iontophoretic methods. The electrokinetic delivery mechanism may also be accompanied by ultrasonic vibration to further facilitate electrokinetic transport of the substance, e.g., by opening pathways in the skin. Ultrasound may be employed in a number of ways such as (i) traditional piezoelectric elements, (ii) magnetostrictive alloys, (iii) Application Specific Integrated Circuits (ASICs) with an ultrasound transmitter built in or (iv) by thin foil sheets with incorporated piezoelectric dipole elements. See, for example, U.S. patent application Ser. No. 09/205,751, filed Dec. 4, 1998, now U.S. Pat. No. 6,385,487, of common assignee herewith, the disclosure of which is incorporated herein by reference.

There are several difficulties with electrokinetic delivery of substances such as medicaments. One is the heretofore need for somewhat cumbersome, bulky and costly equipment which oftentimes requires the presence of an individual at a doctor's office or treatment center and use of medical professionals to administer the medicament. Private, self-administration of medicaments or for diagnostic application by the individual at non-medical or non-professional facilities is highly desirable. Also, an easily transportable apparatus for electrokinetic delivery of medication, for example, a lightweight, compact portable device useful with an applicator packaged as a single or unit dosage applicator, and which may be readily and easily manipulated to contact the treatment site appears ideal as a patient/consumer friendly self-administration system appropriate for many circumstances.

BRIEF DESCRIPTION OF THE INVENTION

In accordance with a preferred embodiment of the present invention, there is provided a portable, self-contained, digit-mounted, lightweight, compact and wireless electrokinetic device or medicator for delivering a substance, e.g., a medicament, for self-administration to a treatment site. By the term substance is meant a medicament as well as natural or homeopathic products that may be outside the definition of medicament, e.g., inks and pigments for tattoos, and more generally includes any substance capable of electrokinetic transport through skin or mucocutaneous membrane, e.g., into a treatment site or from a site, e.g., for diagnostic purposes. The majority of applications using the present invention are for applying medicaments to treatment sites and therefore the terms medicament and substance are used interchangeably, each embracing the other, the term medicament being used in lieu of the term substance throughout this specification for convenience. By medicament is meant any chemical or biologic substance that may be used on or administered to humans or animals as an aid in the diagnosis, treatment or prevention of disease or other abnormal or cosmetic condition or for the relief of pain or to control, diagnose, measure, detoxify or improve any physiologic or pathologic condition. By a treatment site is meant a target tissue, e.g., a diseased tissue, or diagnostic/detoxification site for extraction of a substance, underlying or exposed through or on an individual's skin, cutaneous or mucocutaneous membrane.

In a first aspect of the present invention, an individual may privately self-administer the medicament by employing the self-powered wireless finger-mounted device hereof to electrokinetically drive the medicament into the treatment site, e.g., through the skin or mucocutaneous membrane to a diseased tissue. Preferably, a low-cost digit-mounted device is used to facilitate the flow of medicament into the skin under the influence of the electromotive force supplied to the medicament by the self-powered digit-mounted wireless device. The device is preferably lightweight, compact, inexpensive and portable and comprises a device body or splint configured for mounting on an individual's extremity for self-manipulation and containing a power source, for example, a battery, connected directly or indirectly to first and second terminals and suitable electronics controlling and interfacing with active and counter electrodes. The device is preferably mounted on the individual's finger to facilitate manipulation of the device so that the active electrode connected to the first terminal may be located against the skin or mucocutaneous membrane, i.e., the treatment site. The second terminal of the power source is coupled with the counter electrode, i.e., a tactile electrode, on the surface of the device for electrical contact with a second skin site, e.g., a portion of the individual's finger engaged by the device. The polarity of the active and counter electrodes may be reversed by either a mechanical switch, a relay or solid-state implementation as the application may dictate. By self-manipulation is meant that the individual can mount the device on a finger of one hand or a portion thereof and substantially freely orient the device to engage the active electrode of the device through a substrate containing medicament or a conductive carrier therefor, or directly through medicament interposed between the skin or mucocutaneous membrane and the active electrode, generally wherever the treatment site is located and irrespective of whether a substrate is used and, if used, irrespective of whether the substrate is attached to the device or to the individual's skin or mucocutaneous membrane or interposed therebetween with the device subsequently applied to the substrate.

In a preferred embodiment of the present electrokinetic medicament delivery device, there is provided a substrate having an open cellular structure, for containing the medicament. This preferred open cellular or porous substrate forms a minimum barrier to movement of medicament molecules under the influence of the applied current to electrokinetically transport the medicament molecules into the skin or mucocutaneous membrane. The substrate is preferably pre-filled with a single or unit dose of medicament and pre-packaged with or in an applicator portion of the device prior to application of the device and the attached substrate to the treatment site. It will be appreciated, however, that the substrate can be applied directly to the treatment site or form a substrate interposed between the device, i.e., the active electrode and the treatment site without attachment to the device. For those medicaments which are not per se iontophoretically transportable, the medicament and/or the substrate may be hydrated prior to use or contain a hydrating substance, e.g., water, in prepackaged form containing both the medicament and hydration substance. The hydration substance may contain salts or other ionizable ingredients and is therefore conductive to facilitate electrokinetic transport.

It will be appreciated that upon application of the substrate to the treatment site with the medicament interposed between the active electrode and treatment site, an electrical circuit is completed through the active electrode of the device, the medicament or hydrated medicament in the substrate and the treatment site for return through the individual's skin in electrical contact with the counter electrode of the device. Thus, with the device carried, for example, by the individual's finger in contact with the counter electrode carried by the device, an electrical circuit is completed from the device through the active electrode, the medicament or hydrated medicament, the treatment site, the individual's torso, arm, hand and the tactile electrode. To facilitate completion of the electrical circuit, either or both electrodes may contain or have an overlying layer of an electrically conductive material, for example, hydrogel.

In a preferred embodiment of the present invention, the electrokinetic device is provided in the form of an electrokinetic finger splint medicator, which may be either disposable or reusable or have multiple parts with one part disposable and another part reusable. Preferably, the medicator is releasably secured to the finger of an individual and is preferably provided in two parts: a distal portion mounting an applicator head and a proximal portion mounting a housing for electronics and a power source. The two parts are preferably releasably secured to one another at the time of use. The proximal part contains, inter alia, a power source, various electronics for providing the appropriate electrical current necessary to electrokinetically drive the medicament into the treatment site, finger-mounting securing elements, and electrical contacts. In the preferred embodiment, the proximal part is preferably reusable and may be in either a durable long-term use format or of a more limited time and/or number of uses format, e.g., one year and/or some pre-set, limited number of uses, e.g., five uses, before becoming inoperable, referred to herein as a reposable portion. However it will also be appreciated that the proximal portion may be non-reusable and disposable after only one use. The distal portion preferably carries the active electrode at a location along the outermost end portion of the distal portion and facing outwardly thereof. The substrate containing medicament lies in contact with the active electrode and its opposite planar surface extends at an oblique angle from the underside of the distal portion to facilitate engagement with the treatment site. The counter electrode preferably extends along an inside surface of the distal portion, i.e., opposite the fingerprint portion of the individual's finger respectively. Alternatively or conjunctively, the counter electrode may be located along the underside of the proximal portion. In either case, the counter electrode electrically connects the power source and the individual's finger. When the proximal and distal portions of the medicator are secured to one another, electrical contacts on the proximal and distal portions are electrically connected with one another thus placing the active electrode on the distal portion in electrical contact with the power source and electronics contained in the proximal portion. The counter electrode is also electrically connected with the power source upon securing the distal and proximal portions to one another. Alternatively, an on/off switch may be provided in the electrical circuit whereby, upon securing the distal and proximal portions to one another, the on/off switch may be subsequently switched from the off position to the on position to activate the circuit.

The power source and electronics are preferably carried by and along outermost portions of the proximal portion. The proximal portion is shaped and configured to lie along the finger preferably just forward of the individual's knuckle joint and may extend further back along the back side of the hand. One or more elements for securing the proximal portion to the individual's finger are provided. For example, straps having hook-and-loop fasteners (Velcro®) are preferably provided to secure the medicator proximally to the individual's fingertip. Alternately, as a further example a soft malleable metal arm or arms may be employed to secure the device to the digit. When the distal and proximal portions are secured to one another, the tip of the individual's finger preferably overlies the counter electrode opposite the active electrode.

Preferably, the distal portion has a ring-like or annular configuration for receiving the tip of the individual's finger, the active electrode being housed in an applicator head underlying and electrically insulated from the fingertip or fingerprint portion of the individual's finger. Thus, the active electrode is located in a support or housing carried by the distal portion and has an exposed surface for electrical contact in a separate substrate with (i) a medicament disposed in a porous substrate within or attached to the housing, (ii) medicament in a substrate interposed between the active electrode and the treatment site or (iii) with the medicament per se. With the medicament disposed in a substrate, e.g., a porous pad, applied, fitted or urged into electrical contact with the active electrode or with the medicament applied directly on the active electrode or the treatment site, it will be appreciated that the active electrode of the finger splint medicator can be readily and easily manipulated to engage the medicament, and hydration material if necessary, or substrate carrying the medicament interposed between the active electrode on the medicator against the treatment site.

In accordance with one aspect of the present invention, an electrokinetic delivery system for personal use in self-administration of a medicament to a treatment site on an individual includes a device for releasable securement to an individual's finger and shaped in part to conform to at least a portion of the individual's finger. A retainer releasably secures the device to the individual's finger and a self-contained power source is carried by the device. First and second electrodes are carried by the device. The first electrode is in electrical contact with the power source and is adjacent a distal end portion of the device and adjacent the tip of the individual's finger upon retention of the device on the individual's finger. The second electrode is for electrical contact with a portion of the individual's body and is in electrical contact with the power source. Upon application of the first electrode to a treatment site with the medicament interposed between the first electrode and the treatment site and completion of an electrical circuit through the first electrode, the medicament or conductive carrier therefor, the treatment site, the individual's body, the second electrode and the power source, the device causes an electrical current to flow for electrokinetically driving the medicament into the treatment site.

In accordance with another aspect of the present invention, an electrokinetic delivery system for personal use in self-administration of a medicament to a treatment site on an individual includes a device having a generally ring-shaped body and a through-opening for receiving and releasably retaining the device on the finger of the individual. The device further includes a self-contained power source carried by the device, a first electrode in electrical contact with the power source, and a second electrode for electrical contact with a portion of the individual's body. The second electrode is in electrical contact with the power source. Upon application of the first electrode to a treatment site with the medicament interposed between the first electrode and the treatment site and completion of an electrical circuit through the first electrode, the medicament or conductive carrier therefor, the treatment site, the individual's body, the second electrode and the power source, the device causes an electrical current to flow for electrokinetically driving the medicament into the treatment site.

In accordance with yet another aspect of the present invention, electrokinetic self-administration of a medicament into a treatment site for an individual is provided by: providing a device shaped in part to conform to at least a portion of an individual's finger and having a self-contained power source, first and second electrodes, and a substrate in electrical contact with said first electrode and including an electrokinetically transportable medicament and an exposed contact surface; releasably retaining the device on the individual's finger, with the second electrode in electrical contact with the individual's finger; while the device remains retained on the individual's finger, placing the contact surface of said substrate into contact with the individual's treatment site; and causing electrical current to flow through said first electrode, the medicament or a conductive carrier therefor, the treatment site, the individual's body, said second electrode and said power source to electrokinetically drive the medicament into the treatment site.

In a preferred embodiment according to the present invention, there is provided an electrokinetic delivery system for personal use in self-administration of a medicament to a treatment site on an individual, comprising a device for releasable securement to an individual's finger and shaped in part to conform to at least a portion of the individual's finger, a retainer for releasably securing the device to the individual's finger, a self-contained power source carried by the device, a first electrode carried by the device adjacent a distal end portion thereof and adjacent the tip of the individual's finger upon retention of the device on the individual's finger, the first electrode being in electrical contact with the power source, a second electrode carried by the device for electrical contact with a portion of the individual's body, the second electrode being in electrical contact with the power source whereby, upon application of the first electrode to a treatment site with the medicament interposed between the first electrode and the treatment site and completion of an electrical circuit through the first electrode, the medicament or conductive carrier therefor, the treatment site, the individual's body, the second electrode and the power source, the device causes an electrical current to flow for electrokinetically driving the medicament into the treatment site.

In a further preferred embodiment according to the present invention, there is provided an electrokinetic delivery system for personal use in self-administration of a medicament to a treatment site on an individual, comprising a device having a generally ring-shaped body and a through-opening for receiving and releasably retaining the device on the finger of the individual, a self-contained power source carried by the device, a first electrode carried by the device in electrical contact with the power source, a second electrode carried by the device for electrical contact with a portion of the individual's body, the second electrode being in electrical contact with the power source whereby, upon application of the first electrode to a treatment site with the medicament interposed between the first electrode and the treatment site and completion of an electrical circuit through the first electrode, the medicament or conductive carrier therefor, the treatment site, the individual's body, the second electrode and the power source, the device causes an electrical current to flow for electrokinetically driving the medicament into the treatment site.

In a further preferred embodiment according to the present invention, there is provided a method of treatment by electrokinetic self-administration of a medicament into a treatment site for an individual, comprising providing a device shaped in part to conform to at least a portion of an individual's finger and having a self-contained power source, first and second electrodes, and a substrate in electrical contact with the first electrode and including an electrokinetically transportable medicament and an exposed contact surface, releasably retaining the device on the individual's finger, with the second electrode in electrical contact with the individual's finger, while the device remains retained on the individual's finger, placing the contact surface of the substrate into contact with the individual's treatment site and causing electrical current to flow through the first electrode, the medicament or a conductive carrier therefor, the treatment site, the individual's body, the second electrode and the power source to electrokinetically drive the medicament into the treatment site.

DETAILED DESCRIPTION OF A PREFERRED EMBODIMENT OF THE INVENTION

Figure 1:
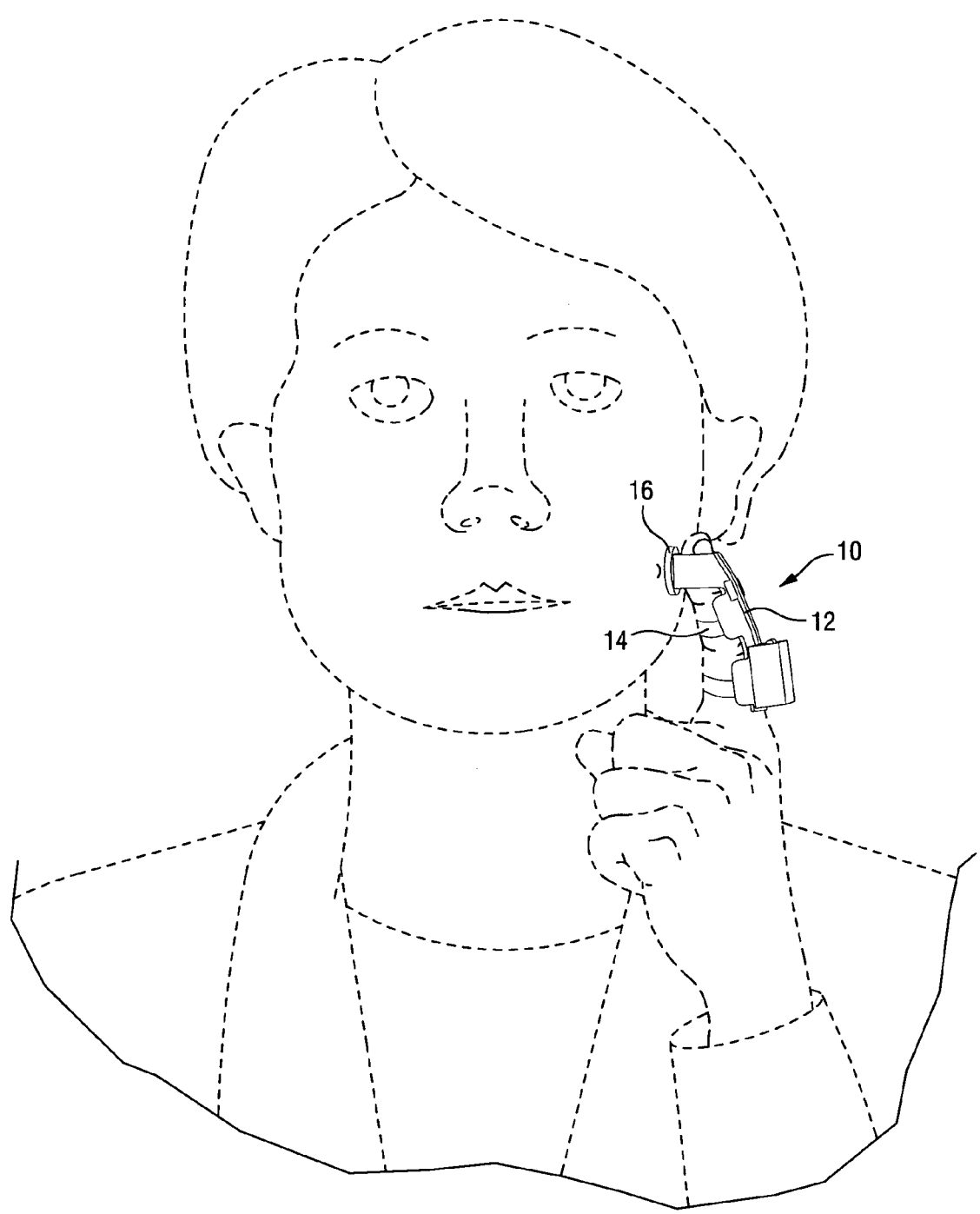
FIG. 1 is a schematic representation of a manner of applying an electrokinetic delivery device according to a preferred embodiment of the present invention to a treatment site.

Referring now to the drawing figures, particularly to FIG. 1, there is illustrated a portable, self-contained, lightweight, compact, finger-mounted, electrokinetic medicament-delivery device or medicator, generally indicated 10 applied to a treatment site on an individual. The device 10 includes a housing 12 mountable to an individual's finger, for example, by straps 14, with a tip 16 of the device 10 mounting an active electrode for driving, i.e., electrokinetically transporting, medicament interposed between the active electrode and the individual's treatment site into the treatment site upon completion of an electrical circuit through the device, the active electrode, the medicament or hydration material carrying the medicament, the individual's body and a counter electrode, i.e., tactile electrode carried by the device. As illustrated, the tip 16 of device 10 housing the active electrode lies adjacent to and underlies the fingerprint portion of the tip of a digit, preferably an index finger, of an individual's hand, enabling the device to be easily manipulated by the individual's arm, hand and finger such that the active electrode at the tip of device 10 may be disposed in overlaying relation to a treatment site with the medicament or medicament-carrying substrate interposed therebetween.

Figure 2:
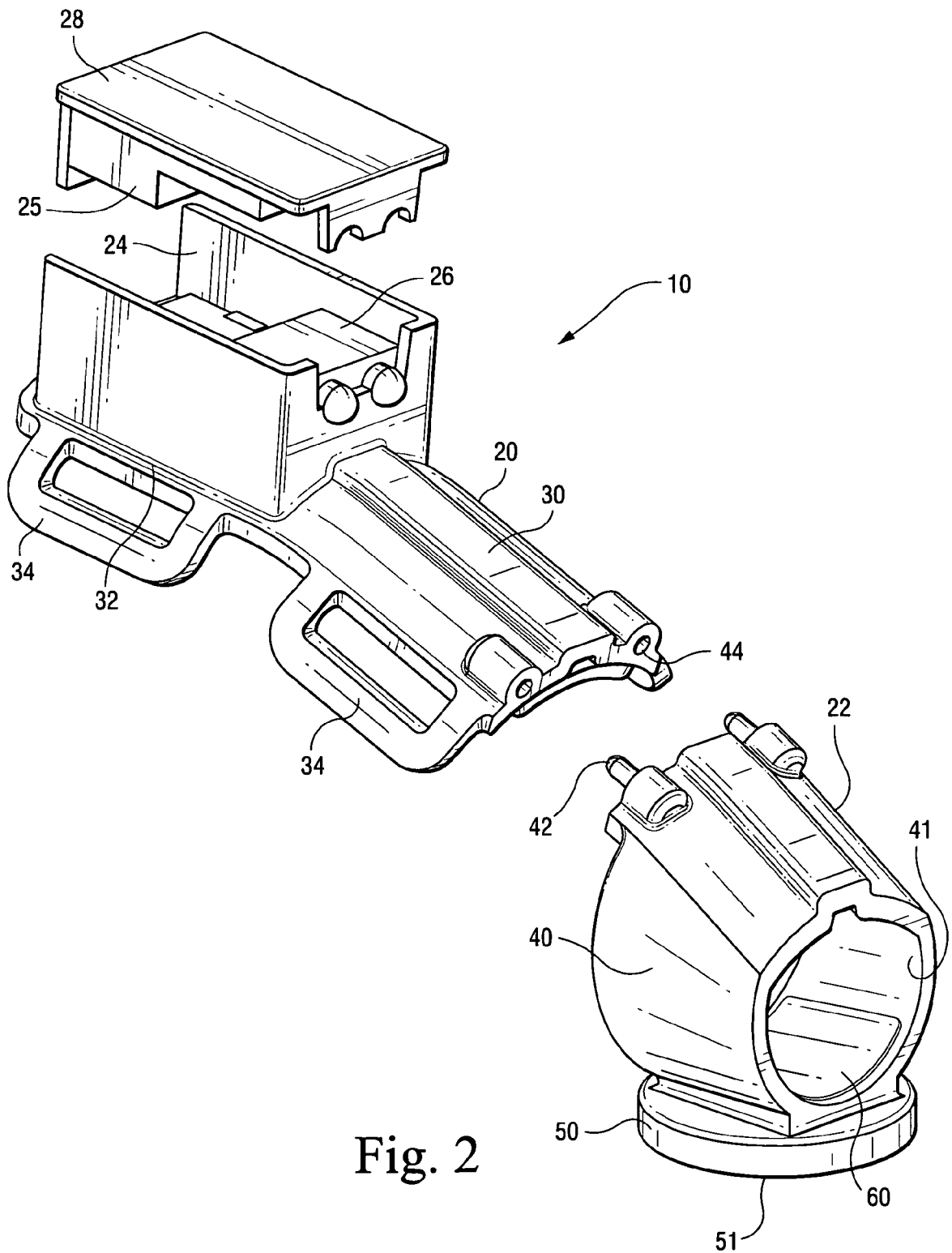
FIG. 2 is an enlarged fragmentary exploded perspective view illustrating the device hereof.

Referring to FIG. 2, the device 10 is preferably provided in two parts: a first part or proximal portion 20 and a second part or distal portion 22. It will be appreciated that the device 10 is substantially rigid in construction, is preferably formed of a plastic material, although other materials may be utilized, and, while a two-part device is preferred, a unitary device or a device formed of more than two parts may be provided. Additionally, while the two parts, when assembled, provide a substantially rigid device, the parts may be interconnected by flexible portions, enabling the device to flex with the flexing of the individual's finger. As explained below, the proximal and distal portions 20 and 22 are connected together to form part of an electrical circuit between an active electrode carried by the distal portion 22, and a power source, tactile electrode and other electronics carried by the proximal portion 20.

The proximal portion 20 includes a compartment 24 for receiving a power source 25, e.g., a 1.5 volt silver oxide battery, as well as an electronics pod 26 for carrying the electronics described below. The compartment 24 may include a removable cover 28 affording access within the compartment. Preferably, however, the compartment is sealed.

Figure 3:
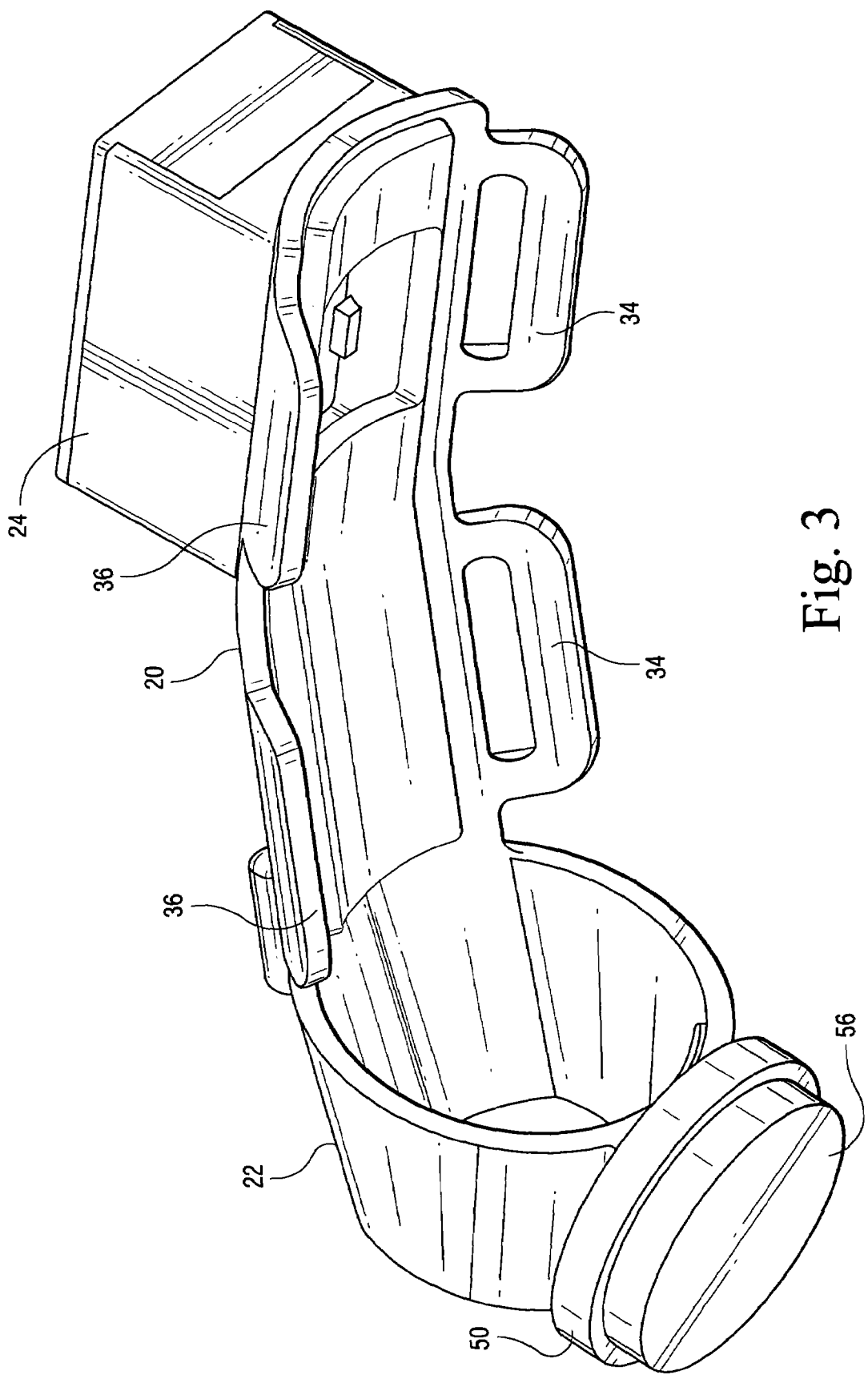
FIG. 3 is a perspective view of a preferred embodiment of the device as viewed from its underside.
Figure 4:
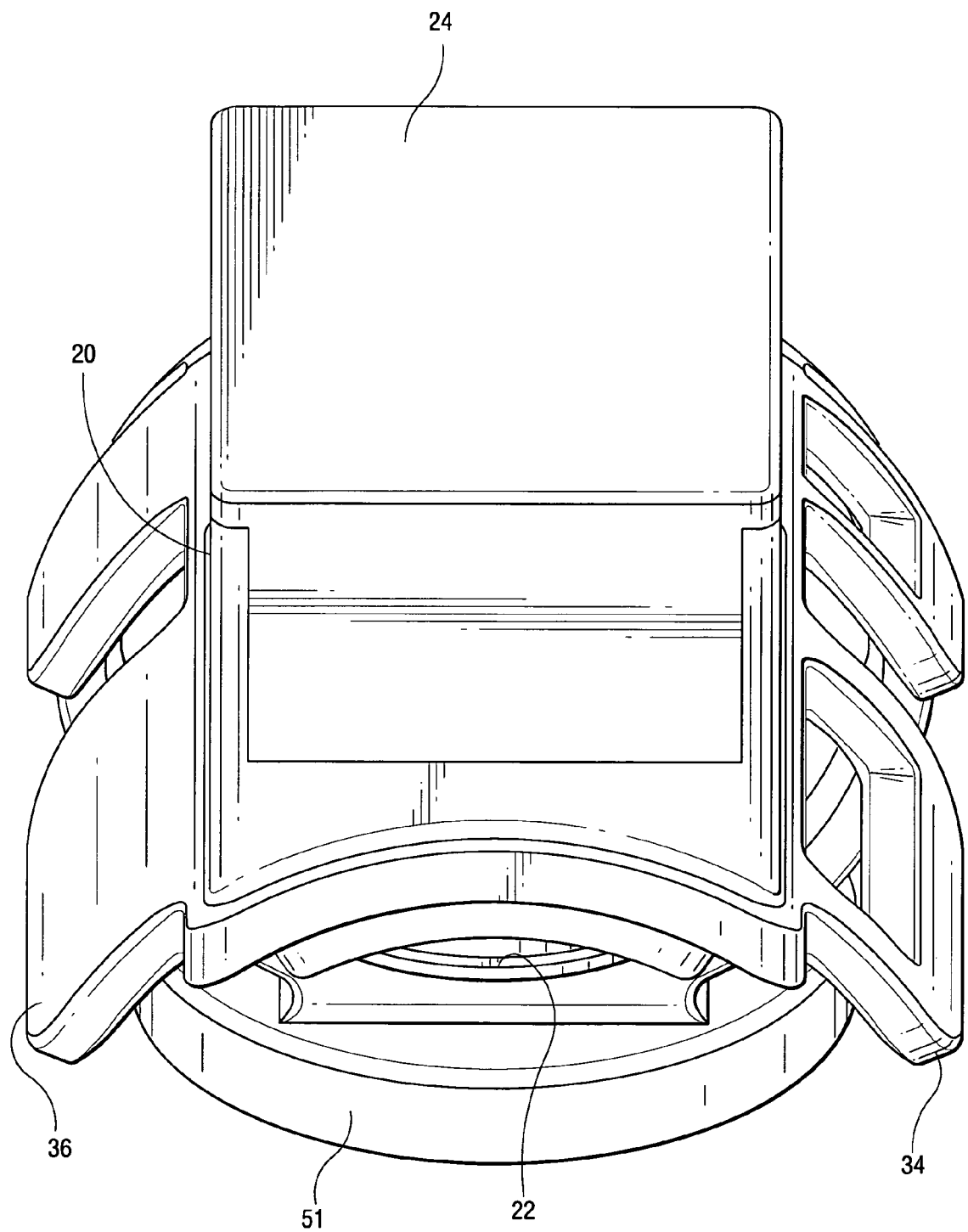
FIG. 4 is an elevational view of the device at a proximal end thereof.
Figure 5:
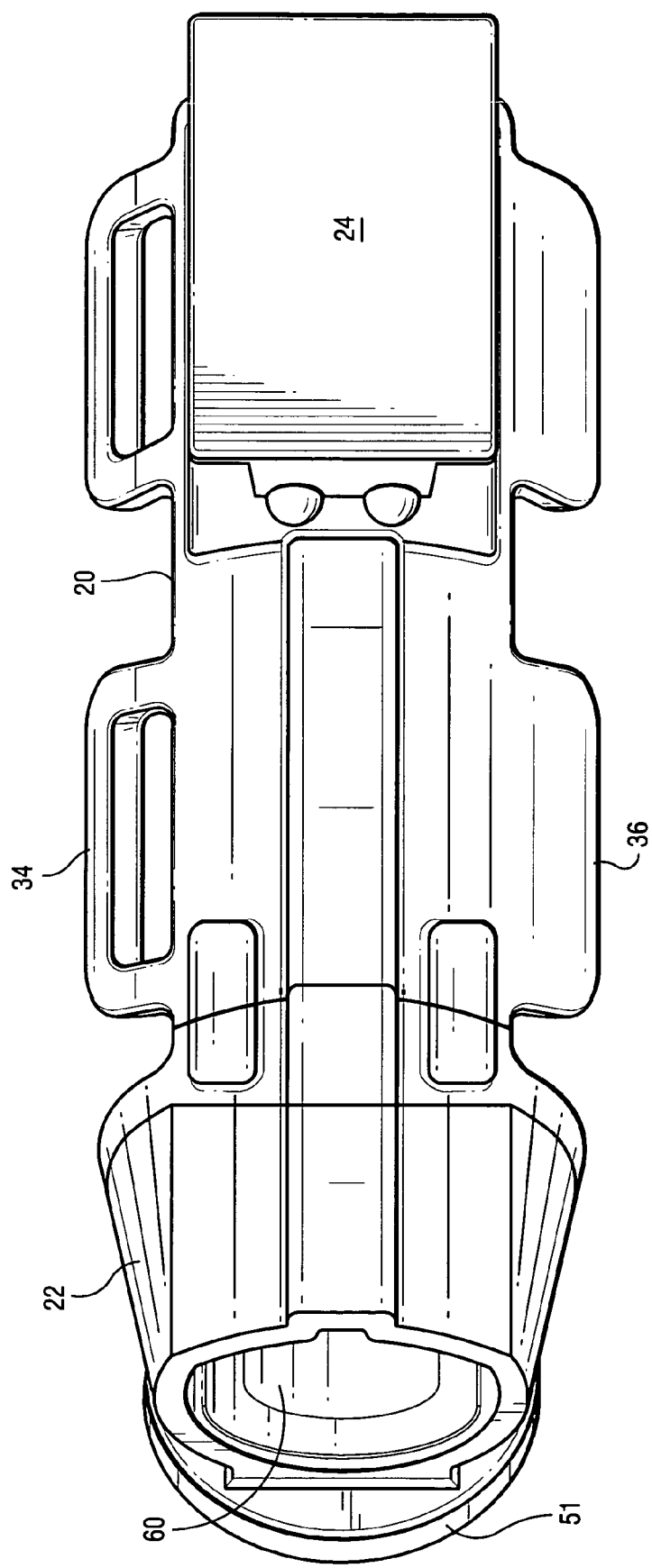
FIG. 5 is a top plan view of the device.

Proximal portion 20 is elongated and shaped and configured to overlie a portion of an individual's finger, preferably an index finger, along opposite sides of the first finger joint, as best illustrated in FIG. 1. That is, forward and rear portions 30 and 32, respectively, of the proximal portion 20 are slightly angled relative to one another to straddle the first finger joint (the joint between the first and second phalanges of a digit) at the apex of the forward and rear portions 30 and 32. Also, the proximal portion 20 has a concave surface along its underside, as best illustrated in FIG. 3, to comfortably overlie and substantially conform to the outer convex portions of the individual's finger on opposite sides of the first finger joint. Adjacent one side and along a margin of proximal portion 20, there are provided a pair of laterally projecting loops 34. Along the opposite margin of proximal portion 20, there are provided a pair of tabs 36. Straps 14 (FIG. 1) are secured in the loops 34. The opposite ends of the straps have one of hook-and-loop fasteners, while the outer surfaces of the tabs 36 carry the other of hook-and-loop fasteners (Velcro®), thereby enabling the device 10 to be releasably secured to an individual's finger. Other means for releasably securing the proximal portion 20 to the individual's finger may be provided. For example, one or more rings or sleeves may be mounted directly to the proximal portion 30 for receiving the individual's finger. Arcuate sections may project from opposite sides of the proximal portion 30 to form one or more resilient split rings for engaging along opposite sides of the individual's finger, their distal ends being spaced from one another along the inside surface of the individual's finger. Elastic straps, buckle-type fasteners, and snap fasteners on elastic or flexible straps may also be utilized. Other types of releasable securements will be apparent to those of skill in this art.

The distal portion 22 of device 10 includes a generally frustoconical section 40 (FIG. 2) sized and configured to receive the tip of an individual's finger, the smaller diameter end of section 40 forming an opening 41 and comprising the outer end of the device. The distal portion 22 may include a closed annular ring as illustrated or a split ring. However, an open-ended frustoconical section having a frustoconical interior surface is preferred because it affords greater control and stability to the active electrode when the medicator is manipulated by the individual to engage the treatment site. Also, the smaller end 41 of the frustoconical section 40 is open to enable the individual's fingertip, including the tip of the individual's nail, to project from the device. It will be appreciated, however, that distal portion 22 may be extended and closed if desired. As illustrated in FIG. 2, a pair of electrical contacts 42 project from the distal portion 22 for engagement in mating electrical sockets 44 formed on the distal end of the proximal portion 20. Thus, when the distal and proximal portions are secured to one another, the power source and electronics of the proximal portion are electrically connected with the active electrode and a counter electrode 60 carried by the distal portion 22. Note also that the juncture of the proximal and distal portions 20 and 22, respectively, lies adjacent the second joint between the second and third phalanges of the digit leaving the third phalange of the digit for reception within the frustoconical interior of the distal portion 22.

Figure 6:
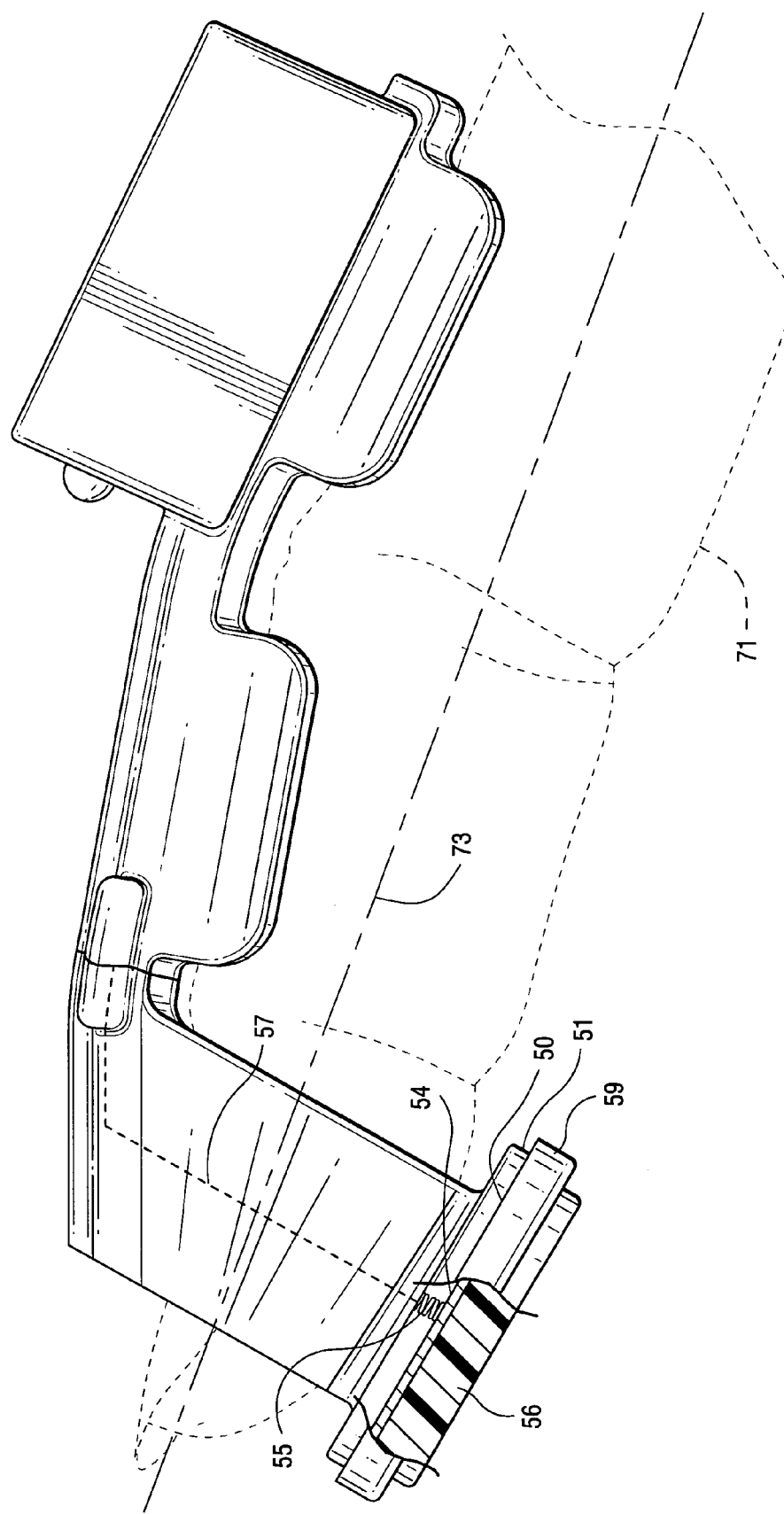
FIG. 6 is a side elevational view thereof.

Referring to FIGS. 3–6, preferably a circular annular housing 50 is provided along the underside of the distal portion 22 and forms part of an applicator head 51 of the distal portion 22. Housing 50 includes an active electrode 54, preferably in the form of a metal disk, mounted at the base of a circular recess 52 (FIG. 6) in housing 50. The active electrode 54 is in electrical contact with the power supply and electronics in the proximal portion 20 when the portions 20 and 22 are connected one with the other. Particularly, a spring 55 in housing 50 interconnects the active electrode 54 and electrical connections 57 within the distal portion 22 in electrical contact with contacts 42 (FIG. 2). As illustrated in FIG. 6, a substrate 56 is disposed in the recess 52, and is preferably formed of a porous, open-cellular, inert material. The substrate material may comprise a non-woven fabric manufactured by Cerex of Pensacola, Fla., identified as Type DN, Group DN07 & DN15. Other suitable types of materials may also be used, provided those materials, at least in the portion of the substrate through which the medicament will be transported to the treatment site, constitute a minimum barrier to the electrokinetic transfer of medicament molecules from the substrate to the treatment site. The substrate 56 preferably conforms to the shape of recess 52, e.g., substantially circular, and may be frictionally maintained within the housing and bearing against active electrode 54. Alternatively, other means may be provided to secure the medicament containing substrate to the housing 50. For example, the recess 52 may include an inwardly directed flange or lip for retaining a substrate within the recess. A preferred embodiment for releasably securing the substrate in the recess 52 in electrical contact with the active electrode 54 is described below with reference to FIG. 7.

Figure 7:
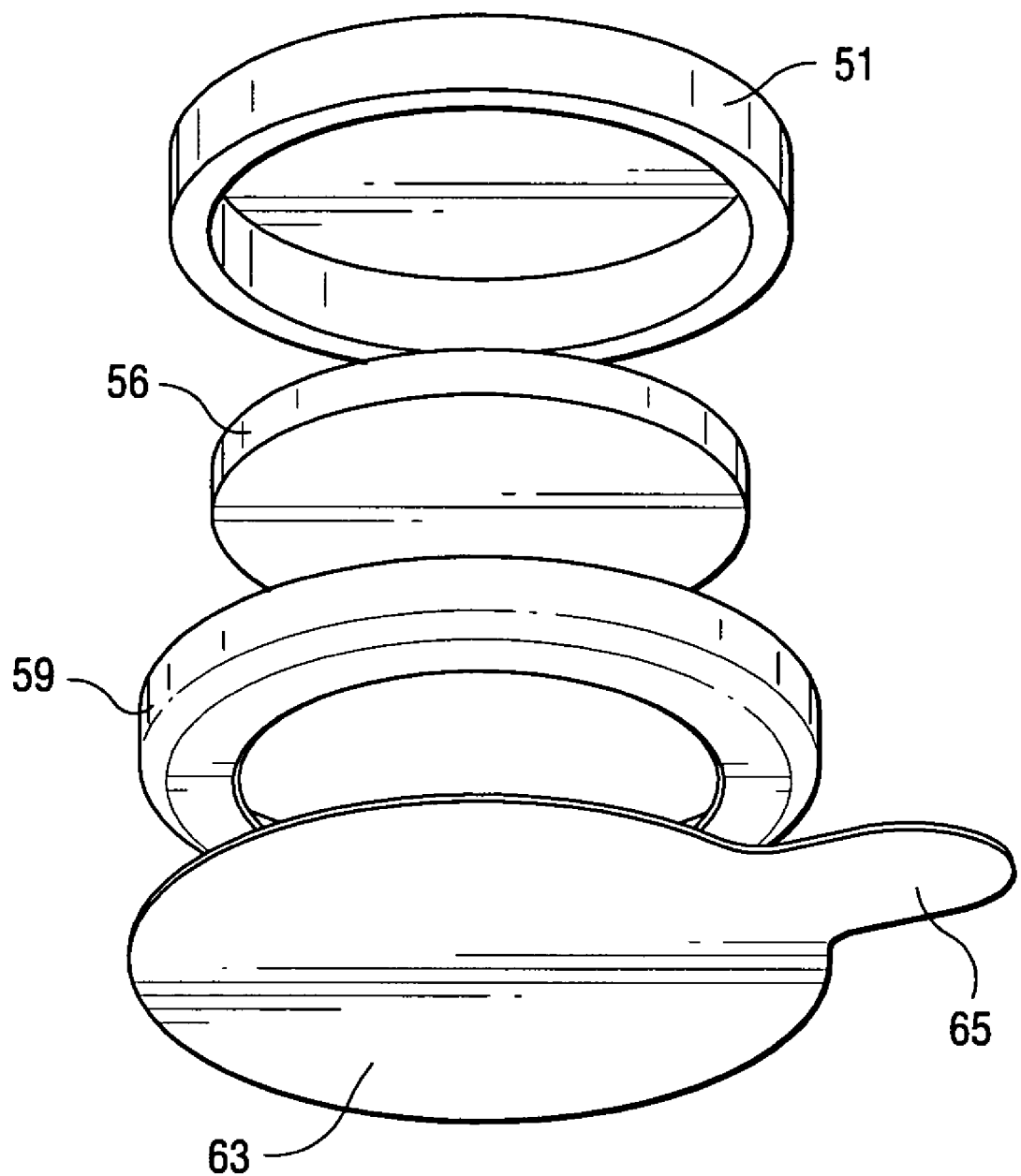
FIG. 7 is an exploded perspective view of a medicated cartridge and the application head to which the cartridge is applied.

It will be appreciated that the substrate 56 may be provided to the user with or without medicament. Thus, when using the finger splint medicator hereof, the user may apply the medicament to the substrate such that the medicament lies within or wicks into the interstices of the material of the substrate. If the applied medicament is not per se conductive, the substrate may also be hydrated by the application of water, for example, by using an eyedropper. In the preferred form, however, a unit dose of the medicament is supplied with and prepackaged in the substrate 56. The medicament permeates the interstices of the porous substrate 56 and the substrate with the medicament is disposed within the recess 52 of the distal portion 22 of the device 10 and factory-sealed. For example, as illustrated in FIG. 7, a retainer ring 59 may overlie the substrate 56 and a release film, e.g., a foil lid 63 having a finger pull or tab 65, may overlie the substrate 56 exposed through the end of the retainer ring 59. By removing the lid 63 prior to use, the medicament permeated in the substrate is exposed for electrokinetic transport into the treatment site.

Alternatively, a unit dose of the medicament may be pre-filled and contained within a rupturable polymer reservoir or capsule within the substrate 56 as in U.S. Pat. No. 5,676,648, issued Oct. 14, 1997, the disclosure of which is incorporated herein by reference. By encapsulating the medicament in a rupturable reservoir or sealing a medicament-permeated substrate, whether within device 10 or separate therefrom, a long shelf-life is assured for medicaments. A non-pre-filled substrate may also be provided the user with the medicament provided separately. In that instance, the user may apply the substrate to the distal portion 22 (if not already contained within housing 50) and either apply the medicament to the substrate before application of the device to the treatment site or interpose the medicament between a suitably hydrated substrate (if auxiliary hydration is required) and the treatment site whereby electrokinetic transport of the medicament into the treatment site can be accomplished. To use the substrate with the encapsulated medicament, the capsule(s) can be opened, for example by peel-away means, such as peeling away a release film, or ruptured by applying pressure to the substrate, for example, by pressing the substrate toward the active electrode 54 after the substrate has been located within the recess 52 of the applicator head either upon manufacture or by the user. By rupturing the capsules, the medicament permeates the interstices of the substrate. If the medicament requires hydration to afford electromotive transport into the treatment site upon application of the electric current, the user may hydrate the pad similarly as previously described. Alternatively, an additional one or more capsules containing hydrating or conductive material, e.g., water or saline, and/or another formulation excipient (s)such as sodium lauryl sulfate with or without cetostearyl alcohol may be prepackaged within the medicament and or substrate.

The substrate 56 is intended for single use only. That is, once the medicament has been electrokinetically driven from the substrate into the treatment site, the distal portion 22 is disconnected from the proximal portion 20 and discarded without the consumer/patient touching the medicament or substrate. It is important to prevent reuse of the distal portion and its used substrate and to render it disposable. For example, active disease particles or other biologic material on the substrate could cause cross-contamination if reused. Insufficient dosage, dehydration or degradation of the medicament could occur if reused. Physical separation of the substrate from the active electrode could occur, rendering dosage or even operability problematical upon reuse. Alternatively, the substrate 56 may be removed from the applicator head 51 and discarded and a new substrate applied to the applicator head. Where the medicament is prepackaged with the substrate either by permeation within the substrate with a release film or foil seal or within a releasable or rupturable capsule within or near the substrate, a coloring agent can be employed, such as iodine, which turns color upon contact with starch in the open-cell material to visibly indicate that a unit dose of medicament has been used. Other types of coloring agents can be used to indicate usage of the applicator, e.g., pH indicators, wet saturation indicators or oxidizable pigments.

Referring to FIG. 6, it will be appreciated that the device 10 is generally elongated and extends generally parallel to the individual's finger 71 when in an extended position as illustrated. The housing 50 extends at an angle relative to the direction of elongation represented by a centerline 73 in FIG. 6 of the device which generally parallels central portions of the individual's finger when extended. Thus, the outer planar face of the active electrode 54 extends at the same angle as the housing relative to the elongated device and faces outwardly and away from the device and the individual's finger. The angle at an intersection between the direction of elongation (centerline 73) and a line through the planar surface of the active electrode 54 is an obtuse angle of approximately 160° but may lie within a range of about 100°–185°. The angular direction of the active electrode relative to the device 10 facilitates application of the device to treatment sites variously located about an individual's body.

Reverting to FIG. 2 and in a preferred embodiment, the counter electrode 60 is located in the distal portion 22 on the bottom of the interior frustoconical surface. Counter electrode 60 may be covered with a conductive material, e.g., water or hydrogel, to facilitate electrical contact with the underside of the individual's fingertip. The counter electrode 60 is electrically insulated from the active electrode. The counter electrode 60 is electrically coupled to the terminal of the battery opposite the battery terminal to which the active electrode 54 is coupled when the distal and proximal portions are electrically interconnected with one another. It will be appreciated that by locating the counter electrode 60 along the inside surface of the distal portion, the act of inserting the individual's fingertip into the opening in the distal portion ensures good electrical contact between the counter electrode and the individual's finger. Alternatively, the counter electrode may be exposed along the underside of the proximal portion 20 for engagement with the individual's finger upon the individual donning the finger splint medicator. In a further alternative, the counter electrode may be located along the underside of both the proximal and distal portions 20 and 22, respectively. Thus, a full-length portion of the individual's finger on opposite sides of the first finger joint and including the fingertip may be in contact with the counter electrode, in either case, affording a good electroconductive contact therewith.

Figure 8:
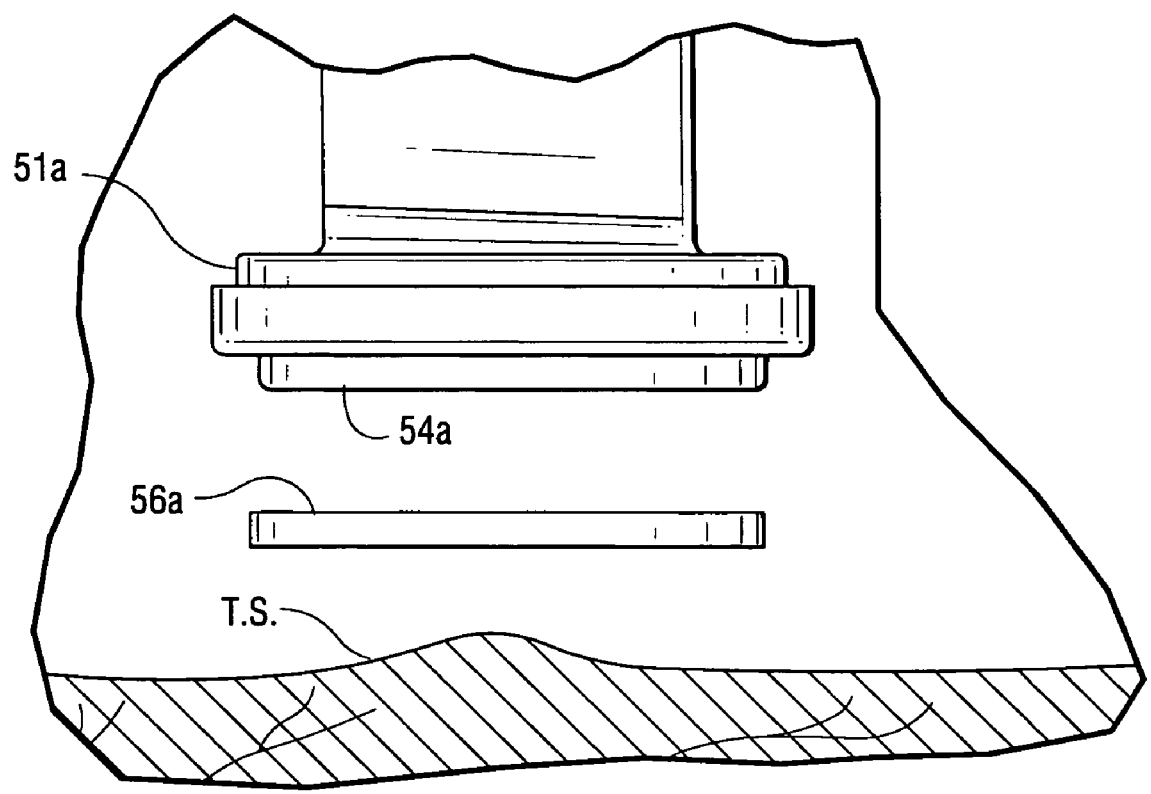
FIG. 8 is a side elevational view of a portion of an applicator head and substrate in accordance with another embodiment hereof.

Referring to FIG. 8, there is illustrated a portion of an applicator head 51a in conjunction with a substrate 56a separate and apart from the device per se. The applicator head 51a is similar to the applicator head 51, except that the active electrode 54a forms a circular projection from the applicator head 51a. Also illustrated in FIG. 8 is a substrate 56a which has been removed from a package, not shown, and which substrate contains the medicament. With the substrate 56a containing the medicament interposed between the active electrode 54a and the treatment site T.S., it will be appreciated that upon completing the electrical circuit by coupling the distal and proximal portions to one another, the medicament in the substrate may be electrokinetically motivated into the treatment site. As a further alternative, the medicament can be applied by a user directly to the treatment site or to a non-prefilled substrate, together with any necessary hydration material, and the circuit completed by applying the active electrode 54a to the medicament or medicament-containing substrate.

The first three stages of Herpes I and II are prodromal, erythema and papule/edema. The preferred treatment with Acyclovir® is to identify and treat the infection in its prodromal stage (no visible signs or symptoms, but individuals feel a tingle or burning or some sensation in the area that breaks out later), i.e., treat optimally with least amount of medicament and shortest application time. Erythema is second (still quite early, with some redness and/or swelling) and is the preferred stage to start treatment if prodromal stage is missed. Papule or edema stage still responds to treatment but not as quickly (skin damage has started to occur with small sores which may be barely visible).

In a preferred form of the present invention, particularly for the treatment of Herpes I and II-type infections, Acyclovir® is the medicament of choice. Acyclovir® may be provided in a cream formulation with approximately 5% comprising the drug Acyclovir®. For example, a 250 milligram formulation of topical cream containing 12.5 milligrams of Acyclovir®, i.e., a 5% formulation, may be utilized. Significantly, this relatively small amount of medicament in the formulation, when applied electrokinetically over a predetermined time duration, affords a therapeutically effective dose. The dosage and time of application may be varied. For example, an approximate 2% formulation of about 4 to 5 milligrams of the active medicament (e.g., Acyclovir®) in a 250 milligram cream formulation applied electrokinetically over a period of no greater than fifteen minutes or an approximate 14–15% formulation, e.g., 37 milligrams in a 250 milligram cream and Acyclovir® formulation, applied electrokinetically for approximately three minutes is believed therapeutically effective. Percentage formulations between 2%–15% over time durations between fifteen minutes and three minutes are believed also to be therapeutically effective. For example, 8%–10% formulations over 5–6 minutes' time duration are also believed therapeutically effective. Thus, using the present device and a small amount of the active medicament applied electrokinetically and locally via the present delivery system has been found effective. While a cream formulation is preferred, it will be appreciated that the topical base may also be a liquid, gel, ointment or lotion.

The formulation for the medicament may also comprise an oil, water, or a combination oil and water, to facilitate penetration of the skin as the excipient(s). For example, oil facilitates penetration of the stratum corneum layer of the skin, while water facilitates penetration of the basal epidermal layer. Thus, a combination of the drug with oil and water included in the formulation is preferred to facilitate penetration of the drug to the treatment site. In a further formulation of Acyclovir®, solvents such as methylene chloride or beta-cyclodextrin may be included to improve water solubility and stability.

The foregoing treatment is also effective for treating Herpes Zoster, Cytomegalovirus (CMV) and additional medicaments of choice may include foscarnet and gancilovir. The device and methods hereof may also be used to provide electrokinetic transport, with or without ultrasound, for tamoxifen citrate, i.e., an antiestrogen, to inhibit Trans Growth Factor $\beta$–1 (TGF$\beta$–1) to suppress estrogen receptors to aid in wound healing and treatment of keloid scar tissue. Also, treatment of eczema with tacrolimus or pimecrolimus as a stand-alone therapy or with steroids is effective. Still further, while Acyclovir® acts on the polymerase enzyme, drug formulations which act on the helicase-primase enzyme are also effective for treating Herpes I and II.

Figure 9:
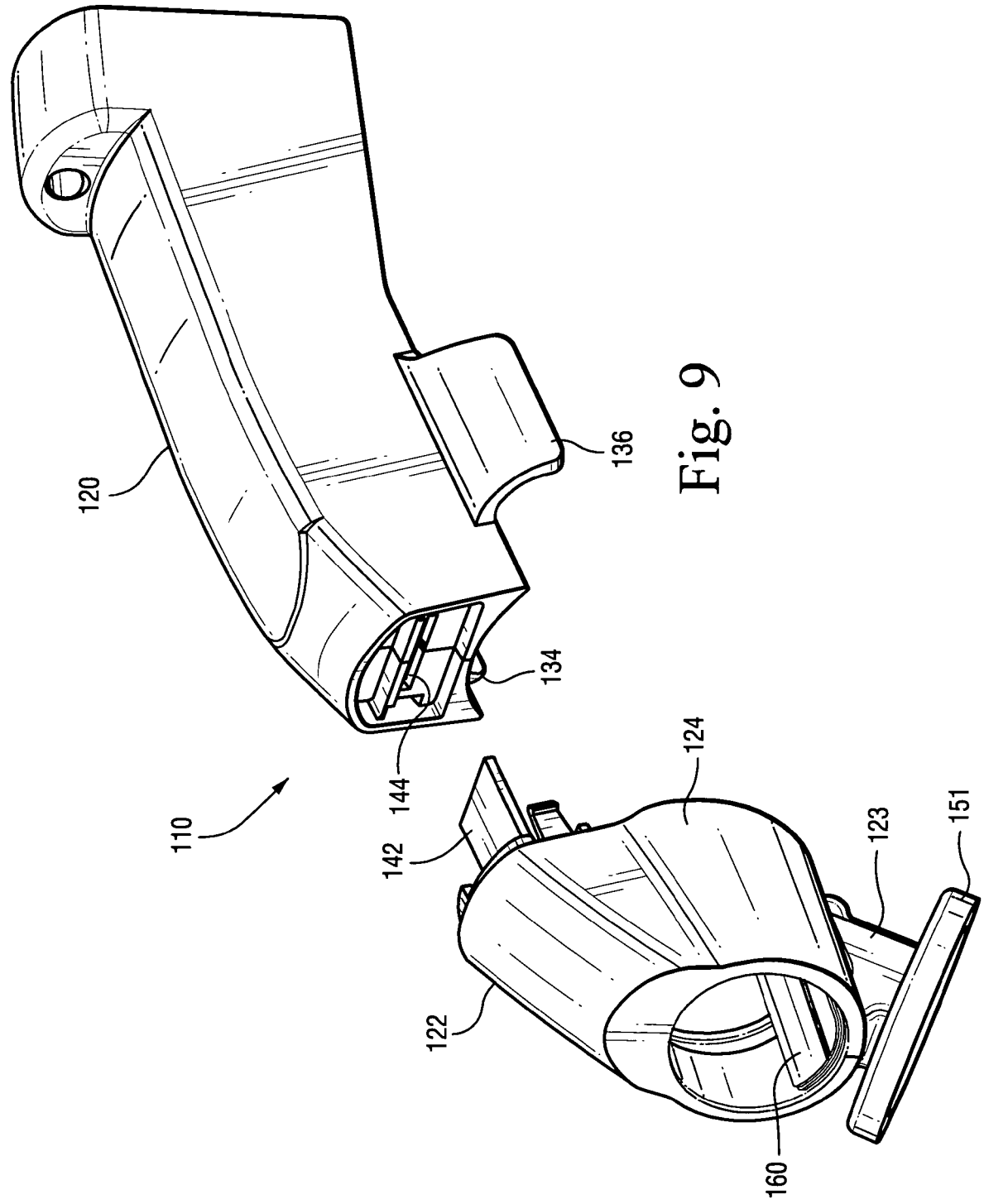
FIGS. 9 and 10 are disassembled and assembled perspective views of an electrokinetic delivery device according to another embodiment hereof.
Figure 10:
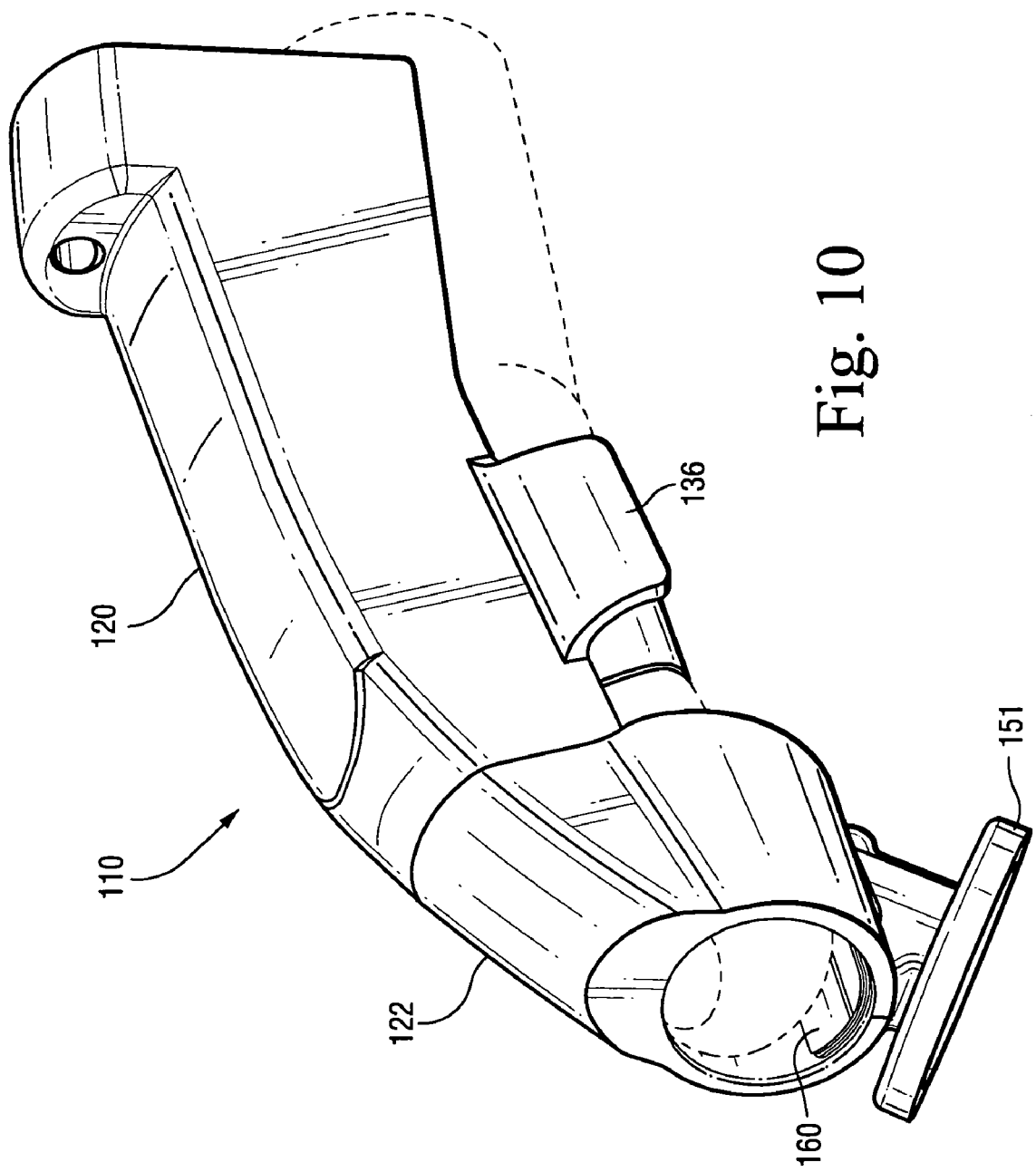

Referring now to FIGS. 9 and 10, there is illustrated a further form of an electrokinetic delivery device according to a preferred embodiment of the present invention wherein like reference numerals are applied to like parts, preceded by the numeral 1. In this form, the device 110 includes proximal and distal portions 120 and 122, respectively, and contacts 142 and 144 in the distal and proximal portions, respectively, for completing the electrical circuit as described herein. The proximal portion 120 includes loops 134 and tabs 136 on opposite sides for securing a strap to the proximal portion and securement of the device to the individual's finger. The proximal portion 120 houses the electronics and power source similarly as the proximal portion 20.

The distal portion 122 is generally frustoconically shaped, as is the distal portion 22 of the prior embodiment, and mounts a pylon or a pair of pylons 123 interconnecting the frustoconical section 124 and the applicator head 151 housing the substrate. The distal portion 122 also carries the counter electrode 160 which, upon interconnection of the proximal and distal portions is electrically connected to the power source and electronics of the proximal portion 120. It will be appreciated that the undersurface of the proximal portion 120 is concave and angled to accommodate the first finger joint and opposite sides thereof for mounting the proximal portion on the individual's finger. Similarly, the distal portion 122 has a frustoconical interior surface for receiving the fingertip of the individual upon electrical and mechanical connection of the proximal and distal portions to one another. In FIG. 10, the device is illustrated in an operable condition applied to an individual's finger, with the individual's fingertip projecting into the distal portion and in electrical contact with the counter electrode 160.

Figure 11:
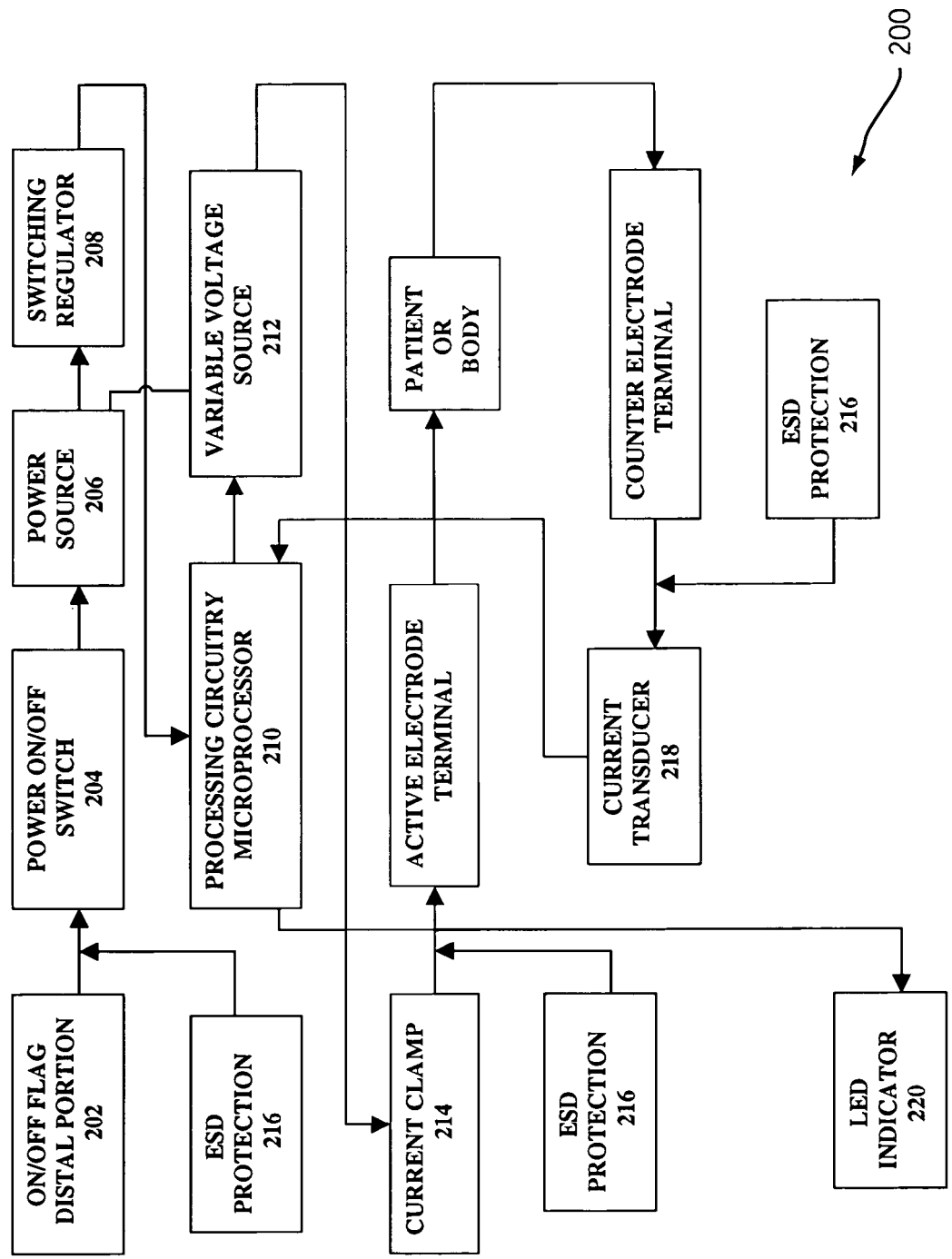
FIG. 11 is a block diagram of an example electrical circuit for the device hereof.

FIG. 11 illustrates a block diagram of representative electrical circuitry 200 for use in the finger splint medicator. Electrical circuitry 200 includes an on/off flag 202, a power on/off switch 204, a power source 206, a switching regulator 208, processing circuitry (microprocessor) 210, a variable voltage source 212, a current clamp 214, electrostatic discharge (ESD) protection circuits 216, a current transducer 218, and light emitting diode or diodes (LED's) 220. The on/off flag 202 is built into the distal portion and may simply include a conducting "flag" surface which completes a circuit of the power on/off switch 204 upon engaging to the proximal portion of the finger splint medicator. The flag surface may, for example, be a thin (e.g., 0.032" thick), copper-clad G10 board with copper on one side thereof. The power on/off switch may simply include two contacts connecting to the power source 206 and to the remaining parts of electrical circuitry 200.

Power source 206 is a battery such as a silver oxide battery having an open-circuit voltage, for example, of 1.55V. The useful life of the battery terminal voltage ranging from 1 to 1.55 V is insufficient to operate circuit elements and components such as processing circuitry 210 and LED's 220. The low battery voltage is tolerated due to the compensation by switching regulator 208, which converts the unsteady and decaying battery voltage to a constant value of, for example, 2.7V.

Skin and tissue resistance largely controls the bias potential required to sustain the treatment current. Other factors include the conductivity of medicament and the resistance between the skin and counter electrode interfaces. A typical range of overall resistance to be encountered is from 5 kohm to 80 kohm. In the most extreme case, a potential of over 30V may be necessary. Variable voltage source 212 converts the low battery voltage to a suitable high output value controlled by a signal from processing circuitry 210. Measurements of the treatment current from current transducer 218 are compared with a desired treatment current for the particular application to obtain an error signal. Processing circuitry 210 increases or decreases the control signal to the variable voltage source 212 with an appropriate digital output signal to reduce and eliminate the measured error signal so as to obtain the minimal necessary instantaneous bias potential for maintenance of the desired treatment current. Current clamp 214 is a redundant safety device used to limit the treatment current to a safe, maximum value (e.g., 450 microamps) under any circumstances.

Electro Static Discharge (ESD) protection circuits 216 (such as one or more diodes) are installed at the entry points of the flag terminal and the positive and negative treatment electrodes, respectively, to protect the internal circuitry from electrostatic damage. The ESD protection circuit for the flag terminal is disposed on the proximal side.

Current transducer 218 converts the instantaneous treatment current to an analog voltage. This voltage is read by the processing circuitry 210 through an internal analog-to-digital (A/D) converter. This digital signal is compared with the selected treatment current value scalable to the reference input voltage of the A/D converter. A digital servo loop is maintained by the processing circuitry 210 to minimize and/or eliminate the error signal between the instantaneous treatment current signal and the current reference. The output of the servo loop is a digital signal converted by an R/C (Resistor/Capacitor) circuit to an analog voltage, which is then used to control the variable voltage source 212.

Processing circuitry 210 performs various tasks including, but not limited to, timing control, current measurement, digital servo of treatment current through feedback control of the bias potential, and illumination of LED or LED's. Processing circuitry 210 may be implemented, for example, as a microprocessor, microcontroller, an application specific integrated circuit (ASIC), a programmable logic array or some combination thereof.

Processing circuitry 210 includes read-only and/or read/write memory. In one example implementation, processing circuitry 210 includes a read/write memory such as an EEPROM. The operations of processing circuitry 210 may be implemented in hardware, software and/or firmware. It is desirable, although not necessary, to reduce and replace hardware elements to the extent possible by using a firmware implementation. Data and instructions for controlling the overall operation of the finger-splint device may be written respectively, to an EEPROM data memory and a flash program memory, and processing circuitry 210 may execute the instructions in response to various signals supplied thereto. These instructions may include instructions for:

monitoring the treatment current and the battery terminal voltage, providing timing control for various treatment phases including the initial standby period (for example, indicated by a flashing green LED), soft-start period, main treatment period (indicated by a constant green LED) and the final soft stop period (indicated by the red LED). The treatment phases need not be the same for all treatments and these phases may vary in some way depending on what is being treated. All the variables, voltage, current, time, electrode size and shape, and the like must be reconsidered and possibly adjusted, illuminating the LED(s) to provide information to the user, exciting a crystal oscillator for accurate timing reference, resetting a watchdog timer to ensure normal software execution, performing a self-consistency check on the accuracy of analog-to-digital converter by measuring the predictable voltage drop across a circuit element (such as an LED) during a short, initial power-up period, and performing servo control of the treatment current by controlling the bias potential generated by the variable voltage source via an output digital signal.

The data stored by the read/write memory within the proximal portion may also include a count indicative of the number of treatment cycles for which the finger-splint device has been used. This count is incremented (or decremented) for each treatment and the device is permanently deactivated after the count reaches a prescribed number indicative of a predetermined number of treatments. For example, a disable flag for disabling processing circuitry 210 may be set in memory when the count on the counter is indicative of the prescribed number of treatments. Alternatively or additionally, various mechanisms for preventing the supply of power to the electrical components may be used to permanently deactivate the device. For example, processing circuitry 210 could generate a signal to burn a fuse when the count on the counter is indicative of the prescribed number of treatments. Similarly, processing circuitry 210 could generate a signal to deliberately damage a transistor or flip a solid state toggle circuit when the count on the counter is indicative of the prescribed number of treatments. It will be readily apparent that other mechanisms (hardware and/or software) may be used and the invention is not limited in this respect.

In another example implementation, the read/write memory may store a total treatment time, which is incremented (or decremented) in accordance with a timer during treatment. When the total treatment time reaches some prescribed total treatment time, the device may be permanently deactivated. Here again, for example, the various hardware and/or software disabling mechanisms described above may be used to permanently deactivate the device.

In still another example implementation, the proximal portion may be disabled from use for a predetermined time period after each use whereby the next use can only occur after the predetermined time period has expired. In this case, a disable flag could be set for the predetermined time period and processing circuitry 210 could prevent operation of the proximal portion when this flag is set.

Also, the distal portion may be deactivated permanently after a single usage. Here again, various mechanisms for prevention of re-use of the distal portion may be used. For example, processing circuitry 210 could generate a signal to burn a fuse incorporated in the distal portion at the end of a treatment. Similarly, processing circuitry 210 could generate a signal to deliberately damage a transistor or flip a solid state toggle circuit incorporated in the distal portion at the end of a treatment. It will be readily apparent that other mechanisms (hardware and/or software) may be used and the invention is not limited in this respect.

Processing circuitry 210 may be programmed with (or have accessible thereto) instructions for a plurality of different types of treatments (e.g., herpes, eczema, acne, boils, blemishes and the like). For example, the desired treatment current, ramp-up/ramp down characteristics and total treatment time for herpes may be different than the desired treatment current, ramp-up/ramp-down characteristics and total treatment time for eczema. The determination of which instructions to use may be based upon a detection (or "recognition") of a particular type of distal portion attached thereto. For example, a distal portion for the treatment of herpes may be configured (either physically or electrically) differently than the distal portion for the treatment of eczema. The configuration of the distal portion is detectable by processing circuitry 210 so that processing circuitry 210 thereafter executes instructions appropriate for the particular type of distal portion connected thereto.

In another implementation, the distal portion may be provided with an interface for interfacing to a computer. Such an interface may, for example, be a serial port, a parallel port, a USB port, an IEEE 1394 port, etc. The interface may take the form of a cradle or docking station into which the distal portion is placed, the cradle or docking station connecting to the computer. The interface to a computer allows the uploading and downloading of data from/to the distal portion. For example, a physician, pharmacist or other health care provider could download to the distal portion instructions appropriate for a particular treatment. Alternatively, an appropriate one of a plurality of different, pre-programmed instruction sets may be selected. Processing circuitry 210 may be programmed to record in memory treatment information (such as the time a treatment took place, the duration of the treatment, the distal portion type connected thereto, etc.). This recorded information may be uploaded to a database containing treatment records for the user via the computer interface.

Assuming appropriate power is available, the distal and/or proximal portion may be provided with additional elements. For example, a small liquid crystal display (LCD) could be provided to the distal or proximal portion to provide a visual output of timing and/or diagnostics. Sound generating circuitry such as a buzzer may also be added to provide aural indications such as warnings, end-of-treatment, etc.

Figure 12:
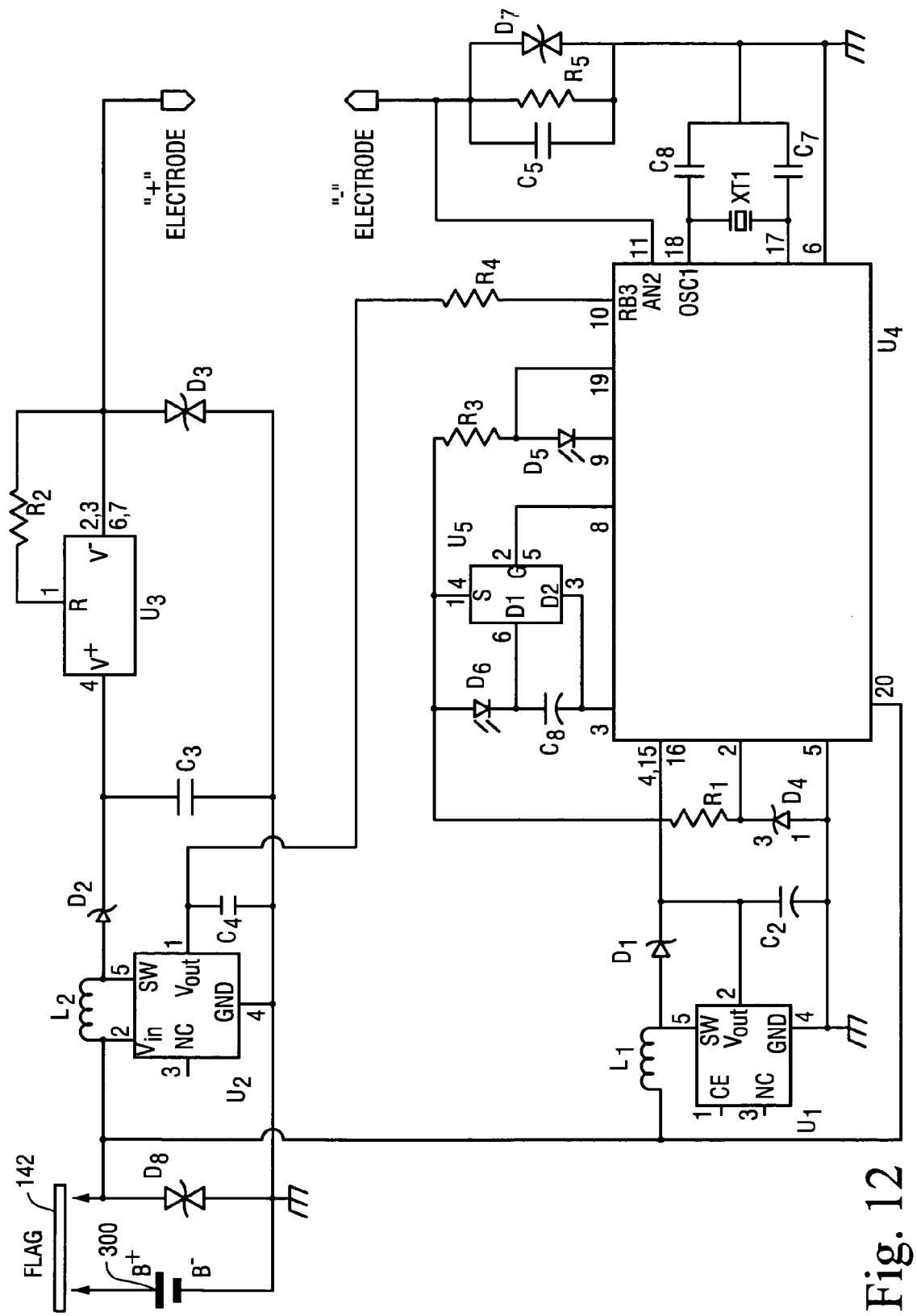
FIG. 12 is a schematic of an example electrical circuit for the device hereof.

FIG. 12 is a schematic showing details of example electrical circuitry 200. Battery 300 corresponds to power source 206 (FIG. 11) and may, for example, have an open-circuit voltage of 1.55V and a rated capacity of 200 mAhr. A suitable battery may be, but is not limited to, EPX76 1.5V silver oxide battery (designation: IEC SR44) available from Eveready Battery Co., Inc. Such a battery would provide for about 10 treatment sessions, if each were ten minutes in length.

Components U1, L1, D1, C1 and C2 correspond to switching regulator 208 (FIG. 11) for converting the battery voltage to a constant value of, for example, 2.7 V. U1 may be, but is not limited to, an NCP1402SN27T1 step-up DC-DC converter (TSOP-5) available from On Semiconductor, Inc. L1 may be, but is not limited to, ELJ-EA470KF, 47 microhenry inductor (SMT-1210) available from Panasonic Industrial Co. D1 may be, but is not limited to, an RB751V40T1 Schottky barrier diode (SOD-323) available from On Semiconductor Inc. C1 and C2 may be, but are not limited to, a 22 microfarad, 4V tantalum capacitor (A case) and a 47 microfarad, 4V tantalum capacitor (B case), respectively.

Component U4 corresponds to processing circuitry 210 and may be, but is not limited to, a PIC16F85 microcontroller (SSOP-20) available from Microchip Technology Inc.

Components U2, L2, D2 and C3 function as variable voltage source 212 (FIG. 11) for converting the low battery voltage to a high output value. U2 may be, but is not limited to, an S-8324D20MC switching regulator (SOT-23-5) available from Seiko Instruments USA. L2 may be, but is not limited to, an ELJ-EA101KF, 100 microhenry inductor available from Panasonic Industrial Co. D2 may be, but is not limited to, an MBR0540T1 Schottky barrier diode (SOD-123) available from On Semiconductor Inc. C3 may be, but is not limited to, a 1 microfarad ceramic capacitor (50V, Y5V, SMT-1206). Variable voltage source 212 is controlled in accordance with a signal from processing circuitry 210. Based on measurements of the treatment current, processing circuitry 210 calculates an appropriate digital output signal to obtain an instantaneous bias potential. Component R4 coupled with C4 functions as a simple digital-to-analog converter. R4 may be, but is not limited to, a 10K ohm, 1% metal film resistor (SMT-0603). C4 may be, but is not limited to, a 0.1 microfarad ceramic capacitor (10V, X7R, SMT-0402).

Components U3 and R2 correspond to current clamp 214 (FIG. 11) and limit the treatment current to a maximum, safe value such as, for example, 450 microamps. U3 may be, but is not limited to, an LM334M current source (SO-8) available from National Semiconductor Corp. R2 may be, but is not limited to, a 150 ohm, 1% metal film resistor (SMT-0603).

D3, D7 and D8 correspond to (ESD) protection circuits 216 (FIG. 11) and D3 comprises 36 V bi-directional voltage suppressor (TVS), which is installed at the positive electrode. This TVS protects internal circuitry from electrostatic damage. D3 may be, but is not limited to, an SMAJ36CA transient voltage suppressor (SMA) available from Diodes Inc. D7 and D8 may be, but are not limited to, a PSD03C 3.3V transient voltage suppressors (SOD-323) available from ProTek Devices.

R5 corresponds to current transducer 218 (FIG. 11) and converts the treatment current to an analog voltage, which is further stabilized by C5. R5 may be, but is not limited to, a 4.99 Kohm, 1% metal film resistor (SMT-0603). C5 may be, but is not limited to, a 0.47 microfarad ceramic capacitor (50V, Z5U, SMT-0805).

Green LED D6 and red LED D5 correspond to LEDs 220. Suitable LED's include, but are not limited to, a green diffused LED and a red diffused LED available from American Bright Optoelectronics Corp. (BL-B22131 and BL-B4531). Green LED D6 remains on during the entire treatment period. The LED normally requires a current limiting resistor for its operation and the resulting power consumption is quite substantial. As shown in FIG. 12, a capacitor C8 switched in accordance with U5 operates as an efficient current limiting device. The situation with red LED D5 is different in that on the rare occasions when it is illuminated, the treatment current is switched off and resistor R3 and the resulting power consumption can be tolerated. U5 may be, but is not limited to, an Si1905DL dual P-channel MOSFET (SC-70-6) available from Vishay Intertechnology Inc.

The electronic circuitry described in connection with FIGS. 11 and 12 is operable so that the finger-splint electrokinetic medicator provides a controlled current for electrokinetically transporting medicament into the treatment site and into the underlying tissue area. The disclosed electronic circuitry provides an effective therapeutic for a skin lesion by incorporating the following features:
- the treatment current is increased and decreased gradually to avoid any uncomfortable sensation of electrical shock, the rise and fall of current may follow a linear ramp or an exponential curve with a long time constant, (e.g., 10 seconds),
- the treatment current per application is accurately controlled by automatic feedback, e.g., maintained at 0.4 milliamperes or less,
- an upper limit of the treatment current is imposed by a stand-by redundant circuit element in order to safeguard against servo loop malfunction,
- minimal bias potential, dictated largely by patient skin resistance, is always applied in order to minimize power consumption,
- ESD protection is implemented for electronic circuitry,
- indicator light(s) are provided for low battery conditions, diagnostics, hardware malfunction, low treatment current, and test completion, therapeutic phase,
- the prescribed treatment time period and automatic test termination are accurately controlled, and
- treatment history is monitored and the device is permanently deactivated after reaching a prescribed length of time and/or number of treatments or uses.

The circuit described in connection with FIGS. 11 and 12 provide these identified features. However, the present invention is not intended to be limited to only circuits that provide for all these features. In addition, it will be appreciated that the specific components and the arrangements thereof shown in FIGS. 11 and 12 are provided by way of example, not limitation. For example, power source 300 may be an adapter for converting power from a conventional wall outlet to power suitable for operation of the finger splint. Alternatively, power source 300 may be a battery that is rechargeable via an adapter connected to a conventional wall outlet. In addition, the electronic circuitry may be adapted to include an alternating current source as described in application Ser. No. 09/523,217, filed on Mar. 10, 2000, the contents of which are incorporated herein by reference, including the hybrid multi-channel design. In still other alternative implementations, the power source may be provided in the distal portion or the distal portion may be provided with a power source to supplement the power source in the proximal portion.

Figure 19A:
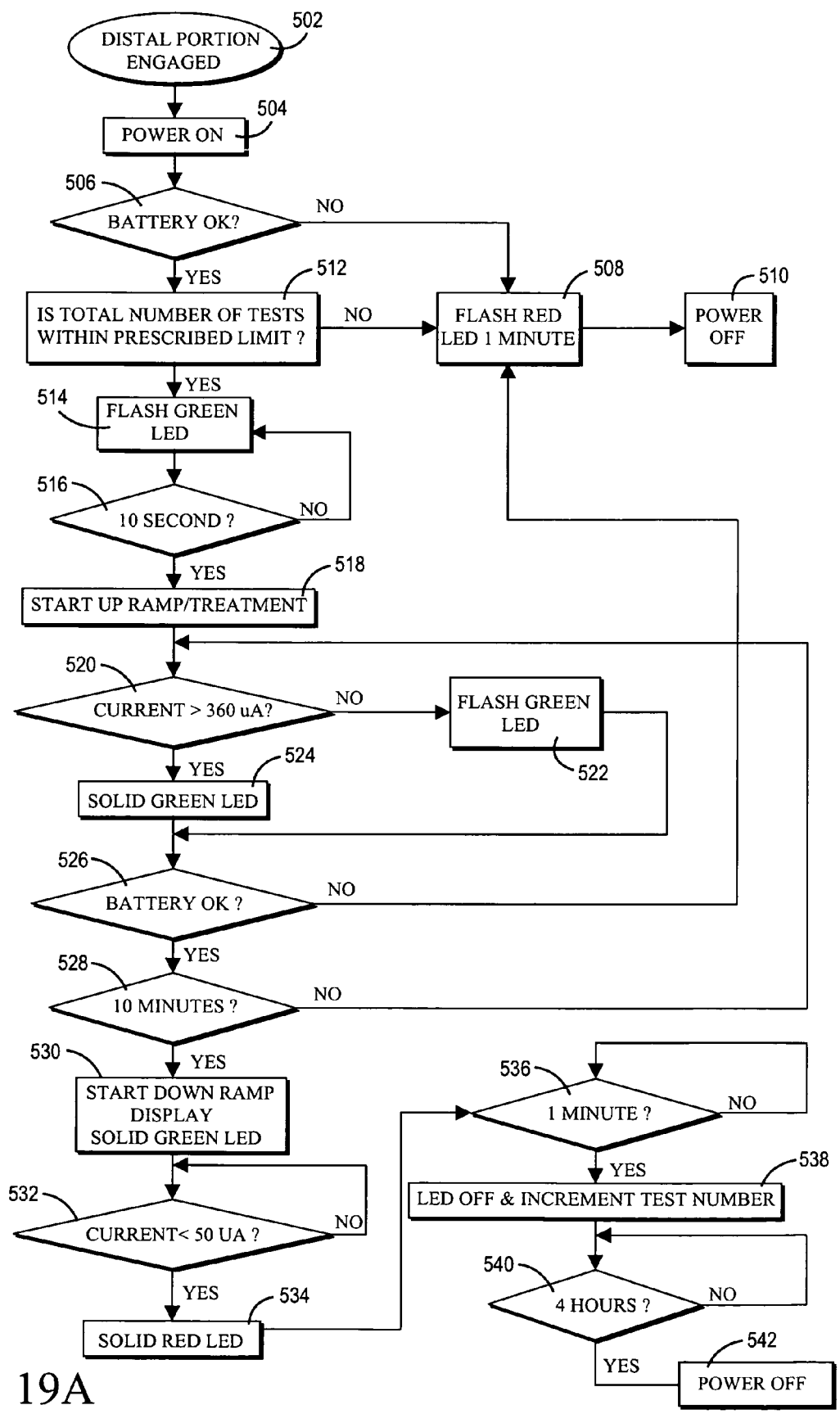
FIGS. 19A and 19B are flow charts illustrating an example operation of the device of FIG. 2.
Figure 19B:
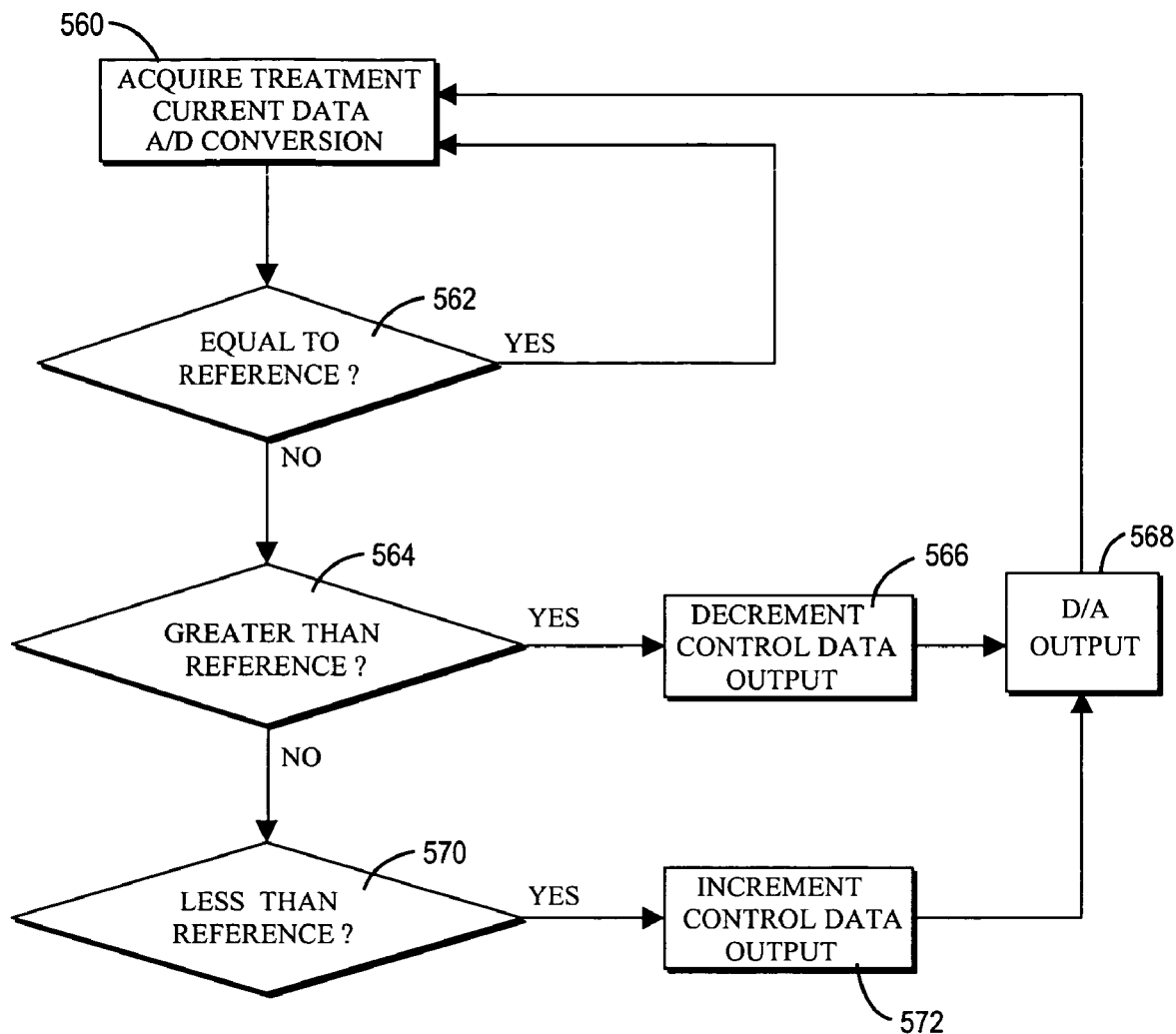

FIGS. 19A and 19B are flow charts illustrating an example operation of the device 10. At step 502, the distal portion 22 is engaged with the proximal portion 20 and power is turned on at step 504 when flag surface 202 completes the circuit of the power on/off switch 204. Processing circuitry 210 performs a battery test operation (step 506) to determine if the battery is okay. If not, the red LED is flashed for a predetermined period of time (e.g., one minute) (step 508) and the power is then switched off (step 510). If the battery is okay, processing circuitry 210 determines whether the number of uses of the proximal portion is less than a prescribed number of uses. If not, the red LED is flashed for a predetermined period of time (step 508) and the power is then switched off (step 510).

If the number of uses is less than the prescribed number, the green LED is flashed for a predetermined period of time (e.g., 10 seconds) (steps 514 and 516). Then, processing circuitry 210 begins to ramp up the treatment current (step 518). After the treatment current is ramped up, treatment begins. During treatment, processing circuitry 210 checks to determine whether the current is greater than 360 microamps. If not, the green LED is flashed (step 522) and the processing circuitry proceeds to the battery test operation (step 526). If the current is greater than 360 microamps, the green LED is kept on (step 524) before proceeding to the battery test operation.

If the battery fails the battery test operation, the red LED is flashed for a predetermined period of time (step 508) and then the power is switched off (step 510). If the battery is okay, processing circuitry 210 determines whether the treatment time period (e.g., 10 minutes) has elapsed. If not, control returns to step 520. If the treatment time period has elapsed, the ramp down of the treatment current begins and the green LED is kept on (step 530). When processing circuitry determines that the treatment current has decreased below 50 microamps (step 532), the red LED is turned on (step 534) and kept on for a predetermined period of time (e.g., one minute) (step 536). After this predetermined period of time, the red LED is turned off and the treatment number is incremented (step 538). After a predetermined period of time elapses (e.g., 4 hours) (step 540), the power is switched off (step 542).

FIG. 19B shows the treatment current servo loop which is executed almost continuously throughout the treatment. At step 560, the treatment current is sampled and converted from an analog value to a digital value. At step 562, a determination is made as to whether the sampled treatment current is equal to the reference treatment current for the current treatment. If so, control returns to step 560 where the treatment current is sampled again.

If the sampled treatment current is not equal to the reference current at step 562, a determination is made at step 564 as to whether the treatment current is greater than the reference current. If so, the control data output of the processing circuit is decreased and this output is converted from a digital value to an analog value at step 568. If the treatment is not greater than the reference current, a determination is made at step 570 as to whether the treatment current is less than the reference current. If so, the control data output of the processing circuit is increased and this output is converted from a digital value to an analog value at step 568.

When using the device 10, 110 hereof, the individual may apply the proximal portion 20, 120 in overlying relation to a finger, preferably the index finger, to be used to apply the medicament to the treatment site. Thus, the proximal portion 20, 120 is overlaid outside portions of the individual's finger, straddling opposite sides of the first knuckle joint and secured thereto by straps 14, 114. The substrate 56, 156 is preferably prepackaged with a unit dose of medicament and supplied within the applicator head of the distal portion 22, 122. If not, the substrate may be applied to the recess 52, 152 of the applicator head on the distal portion 22, 122 of device 10, 110 with or without the medicament. Particularly, the substrate 56, 156 may be inserted into the recess 52, 152 such that the medicament or hydration material within the substrate makes electrical contact with the active electrode 54, 154. If the medicament is electrokinetically transportable and contained in the substrate, the device is ready for use upon connecting the distal portion 22, 122 with the proximal portion 20, 120. Alternatively, if the medicament is not permeated within the substrate, the individual may apply the medicament to the substrate or over the treatment site with suitable hydration material being applied as necessary or desired. Alternatively, if the medicament is provided in a releasable or rupturable capsule in the substrate, the individual may apply pressure to the substrate in the applicator head, rupturing the capsule, enabling the medicament from the capsule to permeate through the open interstices of the porous substrate. If the medicament is not iontophoretically transportable, the substrate may be hydrated by applying water or saline to the substrate.

Once the medicament is enabled for electrokinetic transport, the frustoconical section 40, 140 of the distal portion 22, 122 may be received about the individual's fingertip and contact made with the proximal portion by interconnecting the contacts 42, 142 and 44, 144. By applying the distal portion 22, 122 to the proximal portion 20, 120 and upon application of the applicator head to the treatment site, the electrical circuit is completed. Thus, the electrical circuit includes the active electrode 54, 154, the medicament or the hydration material used to electrokinetically transport the medicament, the treatment site, the individual's body, a return through the counter electrode, the power source and electronics to the active electrode 54, 154.

A treatment program may comprise one or more applications of medicament to a treatment site using the finger splint device described above. For example, a treatment program may comprise five applications of medicament. After each application of medicament, the disposable distal portion is removed from the proximal portion, and a new distal portion is connected to the (re-usable) proximal portion prior to the next application. In some instances, it may be desirable to vary the amount and/or efficacy of the medicament from one application to the next. For example, the amount of medicament used for the first application may be greater than the amount of medicament used for some subsequent application. Thus, a user of the finger splint device may purchase a treatment "package" comprising a plurality of distal portions (e.g., one or more having different amounts of medicament) to be used in a predetermined order. The distal portions may be configured electrically and/or mechanically in a manner that permits the processing circuitry of the proximal portion to detect which distal portion is connected thereto. By way of example, not limitation, the distal portion may include registers readable by the proximal portion. The registers may include information such as, but not limited to, the number of that distal portion in a particular order of use of distal portions. If the processing circuitry is programmed to track the medicament applications (e.g., by incrementing a hardware or software counter as each medicament application is completed), the proximal portion can inform the user (e.g., via the red LED or some other output device such as an LCD if provided) when a wrong distal portion (e.g., an out-of-sequence distal portion) is connected thereto. The detection of the distal portion connected thereto can also be used by the processing circuitry to set a timer fixing an amount of time that must pass before the next medicament application. The proximal portion is disabled to prohibit its use until this time period elapses.

In addition, it will be appreciated that the same proximal portion may be used with more than one type of distal portion. Thus, for example, the proximal portion may be selectively connected to one type of distal portion containing medicament for use in the treatment of herpes or to another type of distal portion containing medicament for use in the treatment of eczema. These distal portions may be configured electrically and/or mechanically so that the processing circuitry of the proximal portion can detect the type of distal portion connected thereto. In response to this detection, the proximal portion can, for example, use operating instructions suitable for a medicament application using the distal portion connected thereto.

The processing circuitry of the proximal portion may be programmed with (or have accessible thereto, e.g., via a memory) a plurality of different treatment current profiles (treatment current versus time), wherein the treatment current profile that is actually used depends upon the distal portion connected thereto. For example, in the case in which a treatment program comprises a plurality of applications of medicament, the treatment current profile for the first medicament application may be different than the treatment current profile for the last medicament application. Similarly, the treatment current profile for a herpes treatment program may be different than the treatment current profile for an eczema treatment program. Here again, the distal portions may be configured electrically and/or mechanically (e.g., using registers on the distal portion) in a manner that permits the processing circuitry of the proximal portion to detect which distal portion is connected thereto. In this way, the processing circuitry can use the treatment current profile appropriate for the proximal portion connected thereto.

Figure 13:
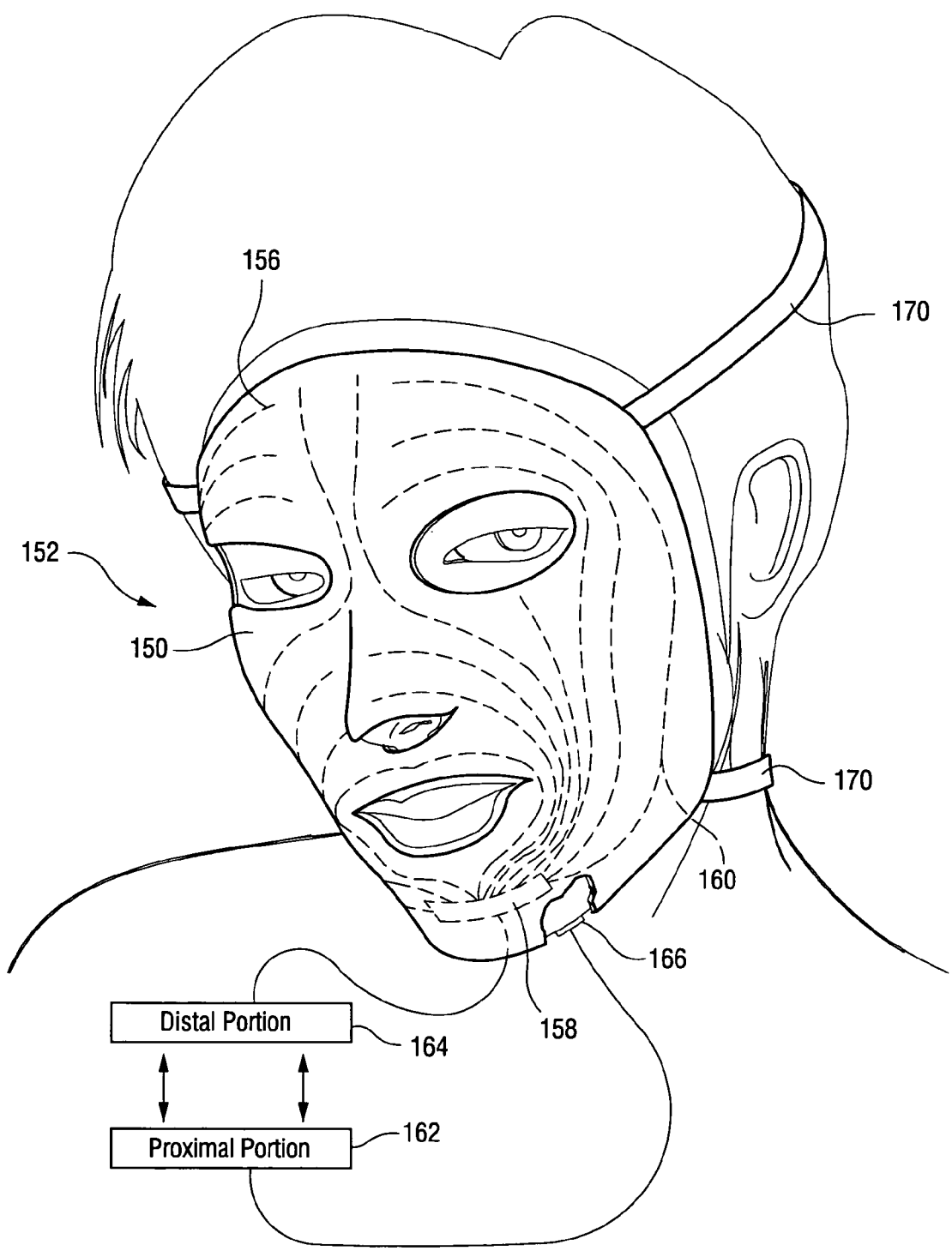
FIG. 13 is a perspective view of a face mask electrokinetic delivery device according to a further preferred embodiment hereof.

Referring now to FIG. 13, there is illustrated a further embodiment of a device for electrokinetically transporting a medicament into the skin and is particularly useful for applying medicament over large wide areas of an individual's face. For example, the illustrated mask, generally designated 150, may be used to treat dermatological conditions, e.g., eczema, psoriasis acne, boils, blemishes, provide anesthesia, or to provide dermal exfoliation. Treatment for wrinkles may be accomplished by delivering a modulator of collagen deposition, an organic nitrate, e.g., gallium nitrate. Treatment with metronidazole for rosecea is also beneficial. In this form of the present invention, there may be provided a full face mask 155 (FIG. 13) or a partial face mask 154 (FIG. 12). The face masks 152 and 154 may be formed of a matrix, e.g., a plastic or fabric material, which may be flexible for providing contact between an underlying medicament-carrying substrate 156. The underlying substrate 156 is formed of a porous material similarly as the substrates previously discussed. The porous material preferably has honeycomb cells which divide the substrate laterally to minimize lateral disbursement of the medicament contained in the substrate.

An electrical connector 158 carried by the mask connects an electrical power source to the mask via a plurality of independent or isolated electrical current channels or lead wires 160 carried by the matrix to form individual electrical conductive channels in the matrix. The current flowing through the channels is separately controlled to prevent tunneling of the current which would adversely affect the user.

The face mask is preferably portable, although it will be appreciated that the power supply can be provided either by an adapter plugged into a conventional electrical current supply or a "tabletop" or "portable" type unit with batteries that may be either disposable or rechargeable. Preferably, however, the power supply may be disposed in a housing portion 162 which corresponds in functionality to the electronics and power source contained in the proximal portion previously discussed. Additionally, another housing portion 164 is adapted for releasably coupling with the portion 162. As in the prior embodiments, connection of housing portions 162 and 164 activates the device. Portions 162 and 164 may serve, in effect, as an on/off switch for activating the device. As illustrated, the proximal portion 162 is electrically coupled to another portion of the face mask through a counter electrode 166. It will be appreciated, however, that the counter electrode 166 may be applied to other parts of the individual's body to complete the electrical circuit. For example, the counter electrode 166 may extend about the periphery of the mask 155 in contact with the individual's skin.

To utilize the electrokinetic device in the form of a face mask, the user dons the mask and attaches the mask to overlie the skin surface on the face by securing straps 170 about the back of the head. It will be appreciated that the substrate contains the medicament to be applied electrokinetically to the individual's face and thus lies in registration with the individual's face. Also note that the electrical conductors or electrodes 160 are closely spaced relative to one another to provide broad coverage, only a small number of the electrodes 160 being illustrated for clarity. Consequently, with the face mask applied as illustrated, the user couples the distal and proximal portions 164 and 162, respectively, to one another, completing the circuit from the power source, through the distal portion, the electrical conductors 160 which electrokinetically motivate the medicament into the facial skin, and the counter electrode for return to the power source. Alternatively, the coupling of the distal and proximal portions may enable the circuit, provided an on/off switch in the circuit is turned "on." A multi-channel system is provided in the face mask and particulars of the multi-channel system are disclosed in U.S. Pat. No. 5,160,316, issued Nov. 3, 1992, the disclosure of which is incorporated herein by reference.

Figure 14:
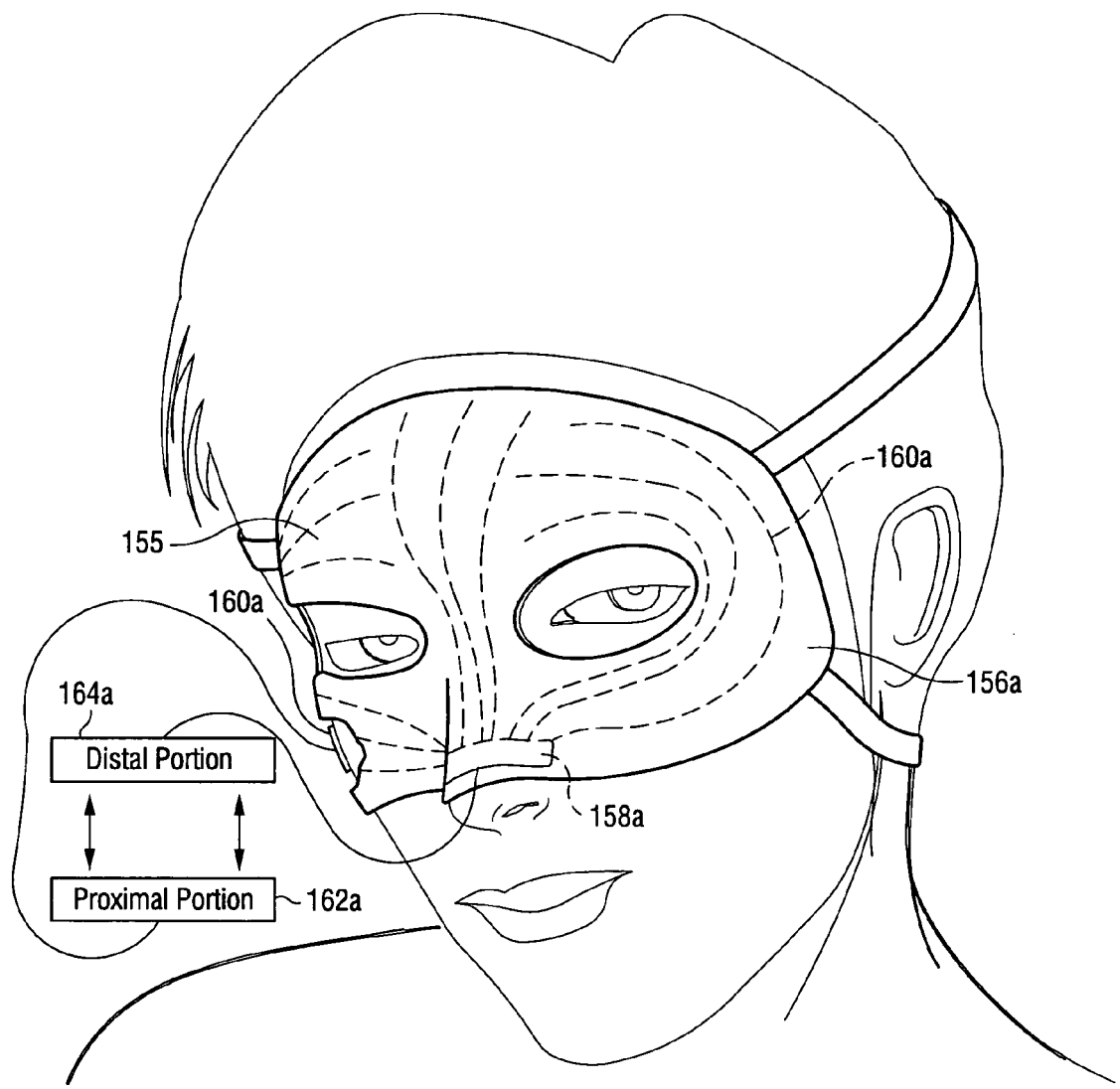
FIG. 14 is a view similar to FIG. 13 illustrating a further form of face mask.

In FIG. 14, like parts as in FIG. 13 are designated by like reference numerals followed by the suffix "a". The mask 155 is abbreviated from that illustrated in FIG. 13 and overlies facial regions about the eyes and nose of the individual and may cover substantially the entire forehead and portions of the cheeks or possibly include the neck or be a separate specific neck treatment applicator. The electromechanical elements of the embodiment are similar to those of FIG. 13 and include the underlying medicament carrying porous substrate 156*a*, electrical connector 158*a*, lead wires 160*a*, proximal and distal portions 162*a* and 164*a*, respectively, and a counter electrode 166*a*. The functionality of these elements is the same as in the previous embodiment.

Figure 15:
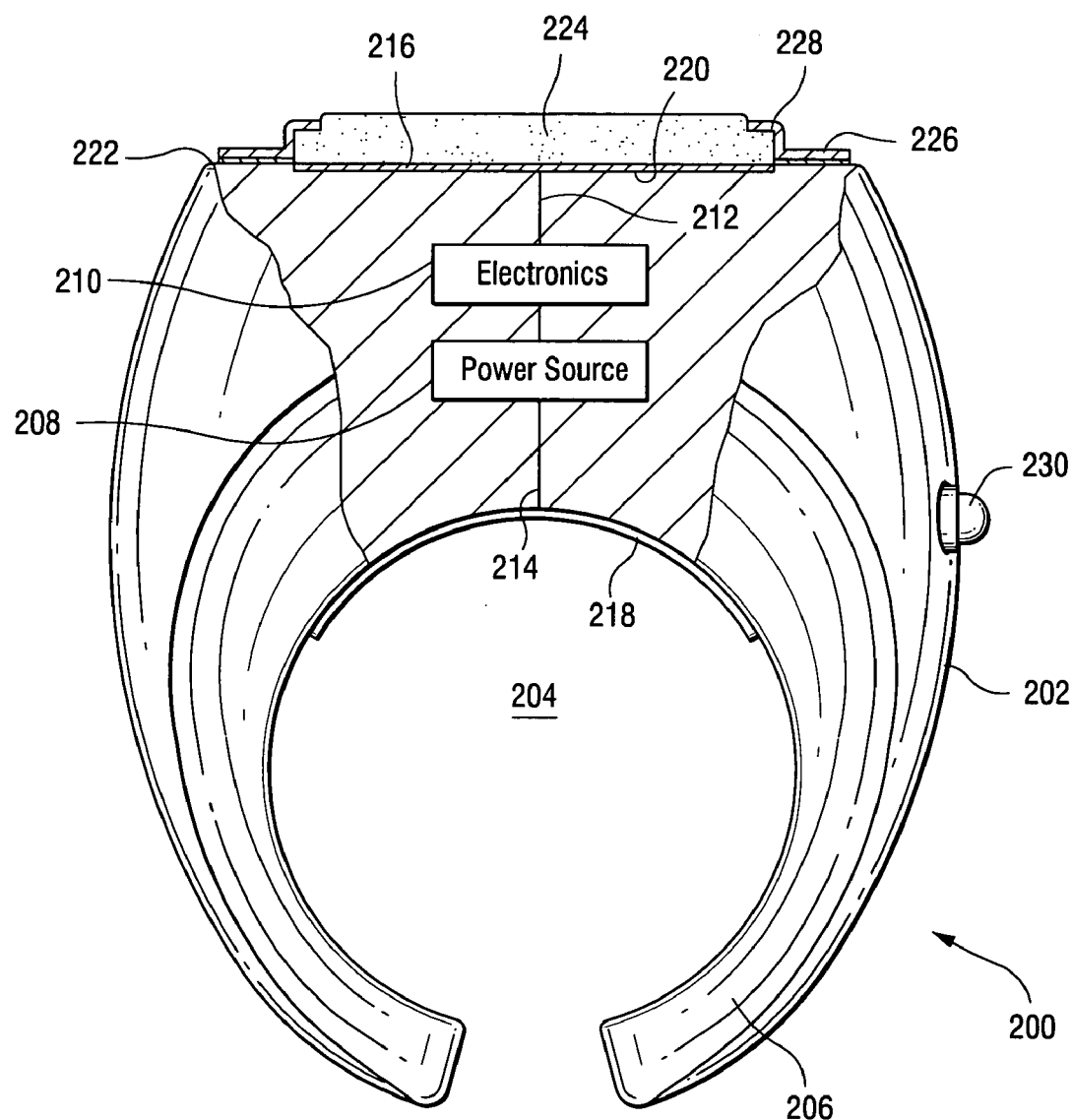
FIG. 15 is a side elevational view of a generally ring-shaped electrokinetic delivery device according to a still further preferred embodiment.
Figure 16:
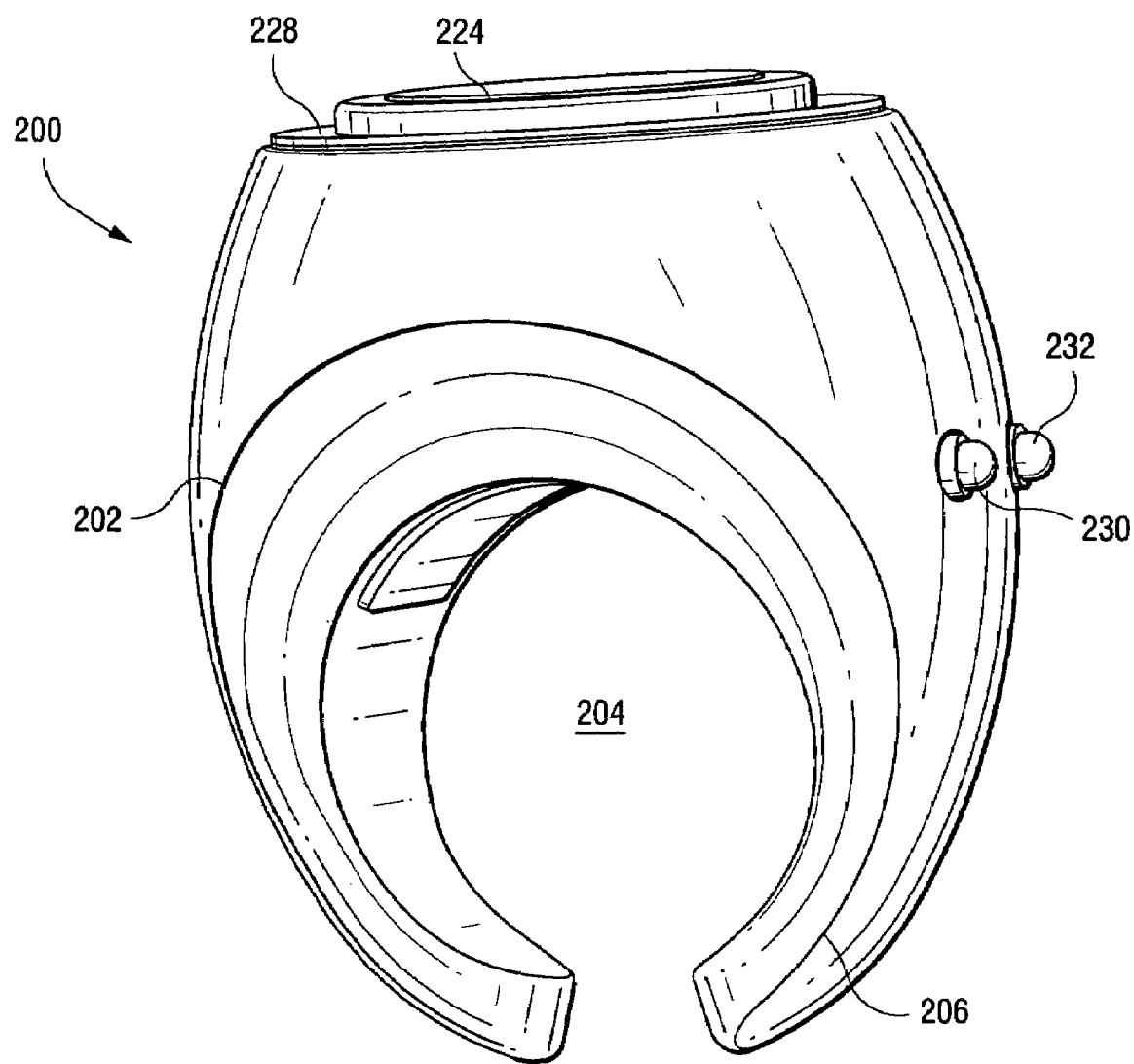
FIG. 16 is a perspective view thereof.

In a further embodiment of the present invention, there is illustrated with reference to FIGS. 15 and 16 a finger-mounted electrokinetic delivery device, generally designated 200, for the self-administration of a medicament and generally in the form of a ring carried by or applied about an individual's finger, preferably the index finger. Ring 200 includes a body 202. The generally ring-shaped body 202 has a through-opening 204 to receive the individual's finger and which opening is flanked by a pair of arcuate sections 206 which, together with a top portion of body 202, form a split ring for maintaining the device 200 on the individual's finger. It will be appreciated, of course, that body 202 may comprise a full circular ring without interruption, although the split ring form is believed preferable to provide flexibility and to accommodate different finger sizes.

The device 200 is self-contained and thus includes within the body 202 a power source 208 and electronics 210, as well as electrical connections 212 and 214 for electrically connecting the power source and electronics to an active electrode 216 and a counter electrode 218, respectively. The power source 208 and electronics 210 are similar to those described previously in the prior embodiments. The active electrode 216 may be in the form of a disk disposed in a recess 220, preferably circular, along the flat outer surface 222 of the ring-shaped body. Overlying the active electrode 216 and in contact therewith is a corresponding generally circular substrate 224 having the same attributes as the substrates 56, 156 previously described. Substrate 224 is maintained on the body 202 by a cap 226 secured to the flat outer surface 222 of the body and having marginal portions 228 overlying margins of the substrate 224. As in the prior embodiments, the substrate 224 contains a unit dose of medicament, and hydration material, if necessary, prepackaged with the device 200 for one-time disposable use. Alternatively, the substrate 224 may be separately packaged with a unit dose of medicament and hydration material, if necessary, apart from device 200 and applied to the device 200 and removed therefrom for each use whereby the device 200 may be reused with successive one-time use prepackaged substrates with medicament. As in previous embodiments, the outer contact surface of the substrate which is to be applied to the treatment site may be overlaid with a foil or releasable film, e.g., as illustrated in FIG. 7, to protect the contact surface and medicament prior to use.

The counter electrode 218 is preferably formed along the inside concave surface of the ring-shaped device 200. It will be appreciated that upon applying the ring-shaped body 202 to the individual's finger, the counter electrode 218 will automatically lie in electrical contact with the individual's finger. That is, the flexible side sections 206 of the device 200 bias the body 202 such that counter electrode 218 is pressed against the individual's finger. As illustrated in FIG. 16, the red and green LED's are indicated 230 and 232 along one side of the device to afford the indications described previously.

To use the device, the ring is disposed about the individual's finger. The device 200 may be provided with an on/off switch to enable the circuit between the active and counter electrodes and through the individual's body. Alternatively, the circuit may be activated in response to application of the ring-shaped body about the individuals finger. For example, the counter electrode 218 may be movable from an outwardly exposed position within the opening 204 to a position lying flush with the interior surface of the ring-shaped body 202 and which movement completes the internal circuit within the body 200 between the active and counter electrodes. With the ring mounted on an individual's finger, it will be appreciated that the substrate can be disposed over a treatment site which completes the electrical circuit through the individual's body and enables electrokinetic transport of the medicament into the treatment site. At the end of the treatment period, the device may be removed from the individual's finger and discarded in its entirety. Alternatively, the device is removed from the individual's finger and substrate may be removed from the ring and replaced by a fresh medicament-containing substrate for subsequent treatment. Of course, if reuse of the device with a fresh substrate is indicated, the on/off switch is placed in the "off" condition or the circuit may be interrupted automatically upon removal of the device from the individual's finger and return of the counter electrode 218 to its projecting position within the opening 204.

Figure 17:
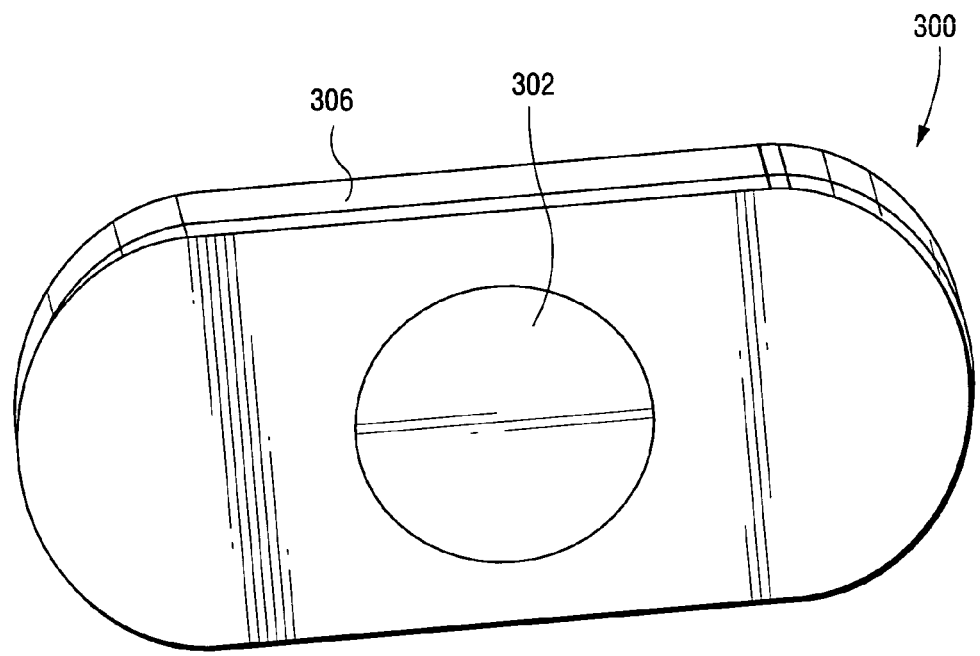
FIGS. 17 and 18 are a bottom view and a side perspective view, respectively, of a patch applicator.
Figure 18:
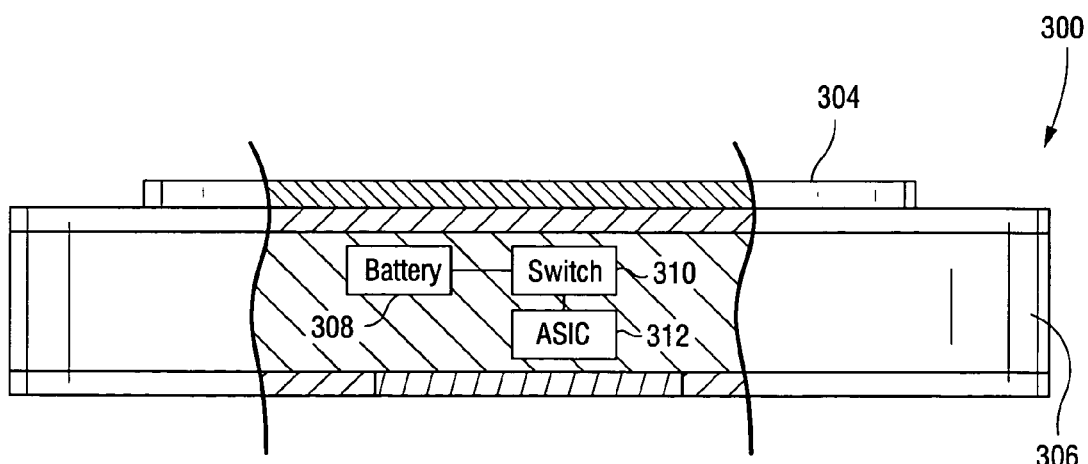

FIGS. 17 and 18 are a bottom view and a side perspective view, respectively, of a patch applicator 300. The patch applicator is intended for limited (one- or two-time) use, after which it is disposed. Patch applicator 300 includes an active electrode 302 and a counter electrode 304. Embedded within the applicator body 306 are a battery 308, a switch 310 and an ASIC 312. Optionally, an LED may be provided. Switch 310 may be a touch-sensitive switch (e.g., membrane) so that the user's finger applied to the counter electrode 304 to hold the applicator in place at the treatment site activates the patch applicator. ASIC 312 controls the treatment current, treatment time, etc. as appropriate for the treatment for which the patch applicator is intended. The optional LED may be illuminated to provide a visual indication that the patch applicator is activated. Alternatively, a non-ultrasound generated vibration can be added or used in lieu of the LED to indicate a working status of the device and that the device lies in a closed current loop via the individual's body surface.

Figure 20A:
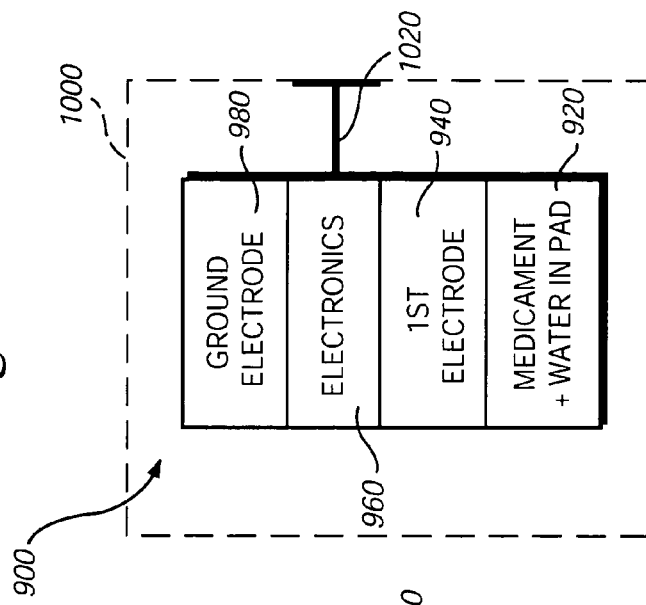
FIGS. 20A–20C are schematic representations of a self-contained applicator illustrating the layers of the applicator within a packaging material.
Figure 20B:
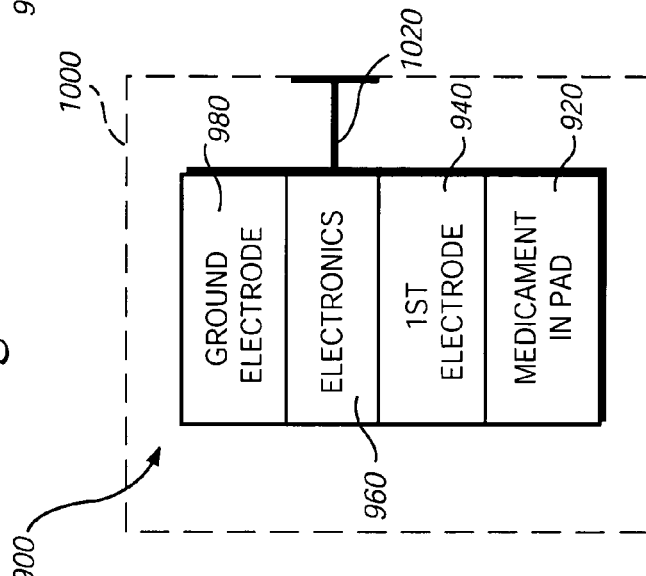
Figure 20C:
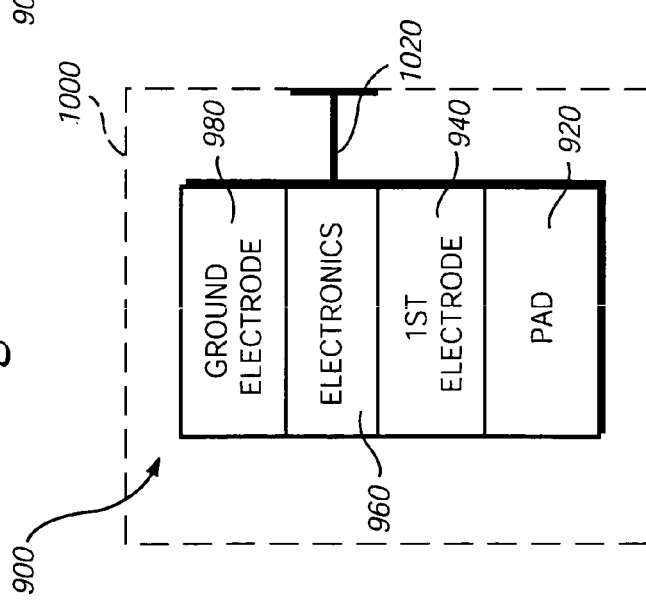

Referring now to FIGS. 20A–20C, there is provided a further form of the applicator hereof comprised of a completely self-contained disposable unit or applicator 900 integrally containing the electronic circuitry and a power source. In this form, the applicator is prepackaged for one-time usage. For example, as illustrated in FIG. 20A, the applicator 900 comprises a pad 920 for containing the medicament and, if necessary, a hydrating fluid. Overlying the pad 920 is the first active electrode 940 electrically connected to electronics 960 within the applicator and which electronics 960 includes a power supply, for example, a battery, and the necessary electronics for flowing a current of a magnitude previously discussed through the pad to electrokinetically drive the medicament into the treatment site. Overlying the electronics is a ground electrode 980, the surface of which remote from pad 920 comprises a tactile surface. Illustrated by the dashed lines is a packaging material 1000, for example, plastic packaging typically employed for sterilized packages whereby the applicator 900 may be sealed within the material 1000. With the medicament prepackaged within the pad 920, the user opens the package 900. In a preferred form, the applicator 900 is connected with the packaging 1000 via a tab 1020. By removing the applicator 900 from or opening the packaging material 1000, the tab 1020 uncovers the battery terminals whereby the power supply is activated. In FIG. 20A, the applicator is provided without the medicament. The user applies the medicament to the pad, hydrates the pad if necessary, and applies the applicator to the treatment site. By applying the pad directly over the treatment site and pressing a finger on the tactile surface of the ground electrode, i.e., on the opposite side of the applicator from the pad, an electrical circuit is completed through the individual's finger and body and through the first electrode, the pad and treatment site whereby the medicament within the pad is electromotively transported to the site. To facilitate good electrical connection, the ground electrode may have an electrical conducting fluid, e.g., hydrogel, overlying its tactile surface.

In FIG. 20B, the medicament is prepackaged in the pad 920. In FIG. 20C, both the medicament and the hydrating fluid is self-contained in the pad. For example, the medicament and the hydrating fluid can be provided in capsules rupturable by pressure applied between the opposite surfaces of the pad before, during or after removal of the applicator from the package 1000. Further, a very weak, e.g., less than 0.05% saline solution encapsulated and integrated between the active foil electrode 940 and the medicament with or without a porous matrix reservoir interposed between the encapsulated hydration fluid and the medicament may be employed. Alternatively, adhesively attached or otherwise releasably attached seals for sealing the medicament and the hydration fluid, if necessary, to the applicator to ensure long shelf life and integrity of the foil electrode can be provided.

Additionally, the unit of FIGS. 20A–20C may have a tacky substance, e.g., hydrogel, not shown, overlying the ground electrode 980 within the package 1000. Upon opening the package, the individual may contact his/her finger on the tacky substance, facilitating removal of the unit from the package 1000. This finger contact on the ground electrode side of the unit also facilitates ready, direct and intuitive manipulation and application of the unit to the treatment site by the individual.

Figure 21:
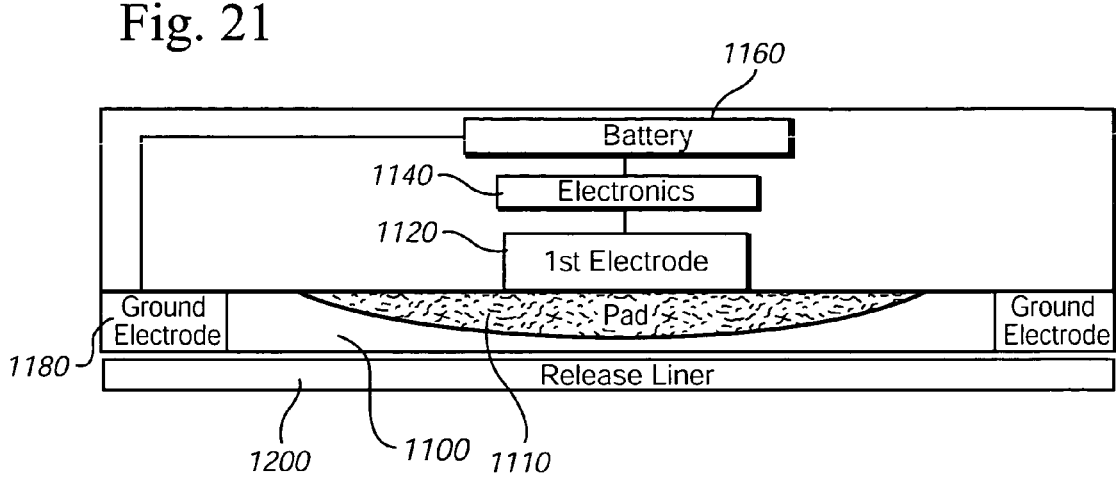
FIG. 21 is a schematic representation of an applicator in accordance with a further embodiment of the present invention.
Figure 22:
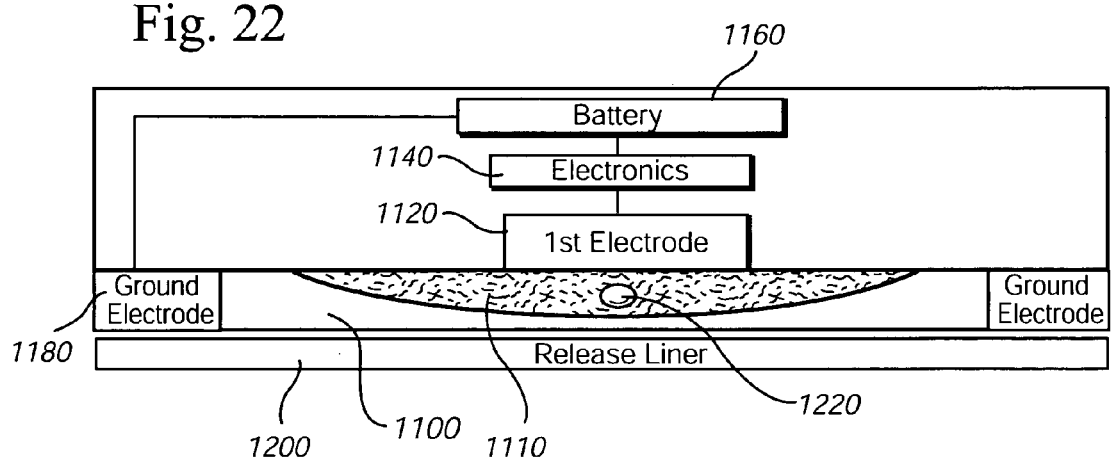
FIGS. 22 and 23 are preferred forms of the applicator of FIG. 21 with an encapsulated medicament illustrated in FIG. 22 and encapsulated medicament and hydrating fluid illustrated in FIG. 23.
Figure 23:
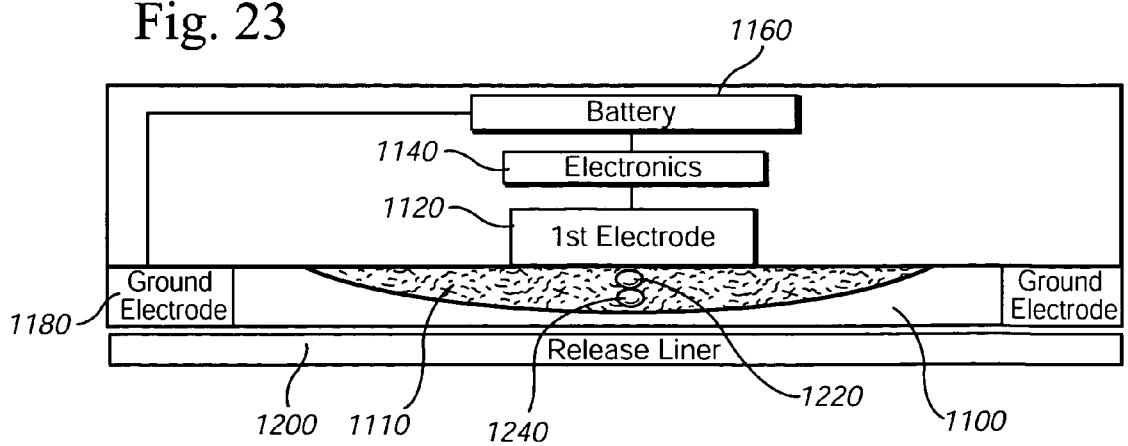

Referring now to the embodiment hereof illustrated in FIGS. 21–23, there is illustrated a further form of applicator body or substrate 1100 which comprises a self-contained disposable unit having integral miniaturized electronic circuitry and a power source. In this form, the applicator may comprise a rectilinear or circular article having a centrally located pad 1110 and electronic circuitry superposed over the pad. Thus, a first or active electrode 1120 overlies the pad and the electronics previously described may overlie the first electrode. The battery 1160 may overlie the electronics. The first terminal of the battery is connected through the electronics with the first electrode which, in turn, is in electrical contact with the pad 1110. The second terminal of the battery is in contact with a ground electrode 1180. The ground electrode may be provided around the margin of the applicator surrounding the pad. For example, if the applicator is shaped in the form of a circle, the ground electrode may comprise an annulus surrounding and electrically insulated from the pad 1110. Alternatively, if the applicator is rectilinear, the ground electrode may comprise the margin of the rectilinear applicator or lie at one end of the applicator. In this form, the electrical circuit is completed between the ground electrode and the pad. The distance between the ground electrode and the pad may be on the order of one-half inch or more. The ground electrode need not surround the pad but may be located to one side of the pad a suitable distance from the pad for completing the return circuit path through the skin between the treatment site and the ground electrode.

In the applicator illustrated in FIG. 21, the pad may be provided without the medicament and the user may apply the medicament to the pad upon removal of release liner 1200. The battery may be of the air-actuated type previously discussed. Thus, the user, upon applying the medicament to the pad and removing the tab from the battery, may apply the applicator over the lesion, holding both the ground electrode about or spaced from the treatment site and the pad in contact with the treatment site. This completes the electrical circuit through the applicator and the individual's skin between the ground contacting surface and pad contacting surface. If desired, adhesive may be provided on the underside of the applicator body 1100 and overlaid by the release liner 1200 to releasably adhere the applicator including the pad 1110 and ground electrode 1180 to the individual's skin and overlying the treatment site. Upon completion of the treatment, the applicator may be discarded.

Alternatively, as illustrated in FIG. 22, the applicator may be prepackaged with the medicament encapsulated within the pad. The capsule is indicated at 1220. If the medicament is itself electrically conductive, the individual may apply pressure to the pad to rupture the capsule, spreading the medicament into the interstices of the pad. This can be accomplished while the applicator remains in its packaging. By applying the applicator to the treatment site similarly as previously described in connection with FIG. 21, the circuit is completed whereby the medicament is electrokinetically driven into the site.

In FIG. 23, both the medicament and a hydrating fluid are encapsulated in the pad. The medicament and hydration fluid capsules are indicated at 1220 and 1240, respectively. The applicator of FIG. 23 is employed similarly as described with respect to FIGS. 21 and 22 after the user ruptures the capsules to intermingle the electrically conductive water and the medicament.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrokinetic delivery system for self-administration of a medicament to a treatment site, comprising:
    an applicator having a self-contained power source, processing circuitry, an active electrode on one side of said applicator and a counter electrode on an opposite side of said applicator, said power source, circuitry and said electrode lying in electrical contact with one another;
    a touch-sensitive switch on the applicator whereby, upon application of the applicator to a treatment site with the medicament or a carrier therefor interposed between the applicator and the treatment site, and application of an individual's finger to said counter electrode to activate the touch-sensitive switch and to maintain the applicator against the treatment site, completion of an electrical circuit through the active electrode, the medicament or a carrier thereof, the treatment site, the individual's body including the finger overlying the counter electrode causes an electrical current to flow for electrokinetically driving the medicament into the treatment site.

2. A system according to claim 1 wherein said applicator contains the medicament.

3. A system according to claim 1 wherein said applicator contains the medicament and said carrier, said carrier comprising conductive hydration fluid.

4. A system according to claim 1 including an LED carried by said applicator for indicating activation of the applicator.

5. A system according to claim 1 including a vibrator responsive to activation of the applicator to indicate a working status of the applicator.

6. A system according to claim 1 wherein said applicator contains the medicament and a seal releasably attached to the applicator to seal the medicament.

7. A system according to claim 1 wherein the active electrode is located on one side of the applicator and a tacky substance is located on the opposite side of the applicator to facilitate manipulation and application of the applicator to the treatment site.

8. A system according to claim 1 wherein the active electrode is located on one side of the applicator and an electrically conductive material is located on the opposite side of the applicator to enable electrical interconnection between the individual's finger and the counter electrode.

9. A system according to claim 8 wherein said electrically conductive material is a tacky substance to facilitate manipulation and application of the applicator to the treatment site.

10. A system according to claim 1 wherein said active electrode, said processing circuitry and said counter electrode are stacked in registration with one another with said active and counter electrodes lying alone respective opposite sides of said applicator.

11. A system according to claim 10 including a medicament on one side of the applicator and a tacky substance located on an opposite side of said applicator with said medicament and said tacky substance being stacked in registration with said electrodes and said processing circuitry and disposed along said opposite sides of said applicator, respectively.

12. A system according to claim 10 including a medicament on one side of the applicator and an electrically conductive material located on the opposite side of said applicator, said medicament, said electrically conductive material and said touch-sensitive switch being stacked in registration with said electrodes and said processing circuitry.

13. A system according to claim 12 wherein said electrically conductive material is a tacky substance to facilitate manipulation and application of the applicator to the treatment site.

14. A system according to claim 1 wherein said processing circuitry includes at least one of a microprocessor, a microcontroller, an ASIC, or a programmable logic array, and a medicament on one side of the applicator and an electrically conductive material located on the opposite side of said applicator, said medicament and said electrically conductive material being stacked in registration with said electrodes and said processing circuitry and disposed along opposite sides of said applicator, respectively.

15. A method of treatment by electrokinetic self-administration of a medicament into a treatment site for an individual, comprising the steps of:
    (a) providing an applicator having a self-contained power supply, an active electrode on one side of the applicator and a counter electrode spaced from the active electrode and lying along an opposite side of said applicator, said active electrode, counter electrode and power supply being electrically coupled to one another;
    (b) applying the applicator to the treatment site;
    (c) placing a finger for electrical contact with the counter electrode on said opposite side of the applicator remote from the one side thereof to complete an electric circuit through the individual's finger, the treatment site, medicament interposed between the active electrode and the treatment site, the active electrode and the counter electrode thereby to electrokinetically drive the medicament into the treatment site.

16. A method according to claim 15 including providing a pad on the applicator on said one side thereof containing the medicament.

17. A method according to claim 15 including providing a pad on the applicator on said one side thereof containing the medicament and a hydrating fluid.

18. A method according to claim 15 including enabling the applicator for one-time use only.

19. A method according to claim 15 including electrically enabling the electrical circuit by providing and pressing a touch-sensitive switch on the applicator.

20. A method according to claim 15 wherein step (a) includes stacking a medicament, said active electrode, said self-contained power supply, said counter electrode and at least one of a tacky substance or an electrically conductive material in registration one over the other with said active and counter electrodes lying along respective opposite sides of the applicator.

21. A method according to claim 15 wherein step (a) includes providing a tacky substance on the side of the applicator remote from the one side thereof to facilitate manipulation and application of the applicator to the treatment site by the individual.

22. A method according to claim 15 wherein step (a) includes providing an electrically conductive material on the side of the applicator remote from the one side thereof to facilitate electrical contact between the individual's finger and the ground electrode.

* * * * *